(12) United States Patent
Lipshutz et al.

(10) Patent No.: US 10,189,016 B2
(45) Date of Patent: Jan. 29, 2019

(54) NANO-TO-NANO FE/PPM PD CATALYSIS OF CROSS-COUPLING REACTIONS IN WATER

(71) Applicant: The Regents of The University of California, Oakland, CA (US)

(72) Inventors: Bruce H. Lipshutz, Santa Barbara, CA (US); Sachin Handa, Louisville, KY (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/624,400

(22) Filed: Jun. 15, 2017

(65) Prior Publication Data

US 2017/0341069 A1    Nov. 30, 2017

Related U.S. Application Data

(63) Continuation of application No. 15/158,238, filed on May 18, 2016, now abandoned.
(Continued)

(51) Int. Cl.

| | | |
|---|---|---|
| *B01J 31/24* | (2006.01) | |
| *B01J 31/06* | (2006.01) | |
| *B01J 31/02* | (2006.01) | |
| *B01J 23/89* | (2006.01) | |
| *B01J 37/16* | (2006.01) | |
| *B01J 31/22* | (2006.01) | |
| *B01J 35/12* | (2006.01) | |
| *B01J 35/00* | (2006.01) | |
| *C07B 37/04* | (2006.01) | |
| *C07C 319/20* | (2006.01) | |
| *C07C 41/30* | (2006.01) | |
| *C07C 45/68* | (2006.01) | |
| *C07D 405/04* | (2006.01) | |
| *C07D 401/04* | (2006.01) | |

(Continued)

(52) U.S. Cl.
CPC ....... *B01J 31/2404* (2013.01); *B01J 23/8906* (2013.01); *B01J 31/0202* (2013.01); *B01J 31/0209* (2013.01); *B01J 31/068* (2013.01); *B01J 31/22* (2013.01); *B01J 35/0013* (2013.01); *B01J 35/12* (2013.01); *B01J 37/16* (2013.01); *C07B 37/04* (2013.01); *C07C 41/30* (2013.01); *C07C 45/68* (2013.01); *C07C 201/12* (2013.01); *C07C 205/12* (2013.01); *C07C 209/325* (2013.01); *C07C 209/68* (2013.01); *C07C 211/45* (2013.01); *C07C 269/06* (2013.01); *C07C 319/20* (2013.01); *C07D 211/70* (2013.01); *C07D 213/30* (2013.01); *C07D 213/64* (2013.01); *C07D 215/06* (2013.01); *C07D 239/26* (2013.01); *C07D 239/54* (2013.01); *C07D 241/18* (2013.01); *C07D 317/22* (2013.01); *C07D 317/46* (2013.01); *C07D 333/60* (2013.01); *C07D 401/04* (2013.01); *C07D 403/04* (2013.01); *C07D 405/04* (2013.01); *C07D 405/14* (2013.01); *C07D 409/04* (2013.01); *C07D 471/04* (2013.01); *B01J 2231/4211* (2013.01); *B01J 2231/4227* (2013.01); *B01J 2231/4266* (2013.01); *B01J 2231/64* (2013.01); *B01J 2531/004* (2013.01); *B01J 2531/007* (2013.01); *B01J 2531/824* (2013.01); *B01J 2531/842* (2013.01); *B01J 2531/96* (2013.01); *B01J 2531/985* (2013.01); *C07C 2603/24* (2017.05)

(58) Field of Classification Search
CPC ........ B01J 2231/4211; B01J 2231/4227; B01J 2231/4266; B01J 2231/64; B01J 23/8906; B01J 2531/004; B01J 2531/007; B01J 2531/824; B01J 2531/842; B01J 2531/96; B01J 2531/985; B01J 31/0202; B01J 31/0209; B01J 31/068; B01J 31/22; B01J 31/2404; B01J 35/0013; B01J 35/12; B01J 37/16; C07B 37/04; C07C 201/12; C07C 205/12; C07C 209/325; C07C 209/68; C07C 211/45; C07C 2603/24; C07C 269/06; C07C 319/20; C07C 41/30; C07C 45/68; C07D 211/70; C07D 213/30; C07D 213/64; C07D 213/06; C07D 239/26; C07D 239/54; C07D 241/18; C07D 317/22; C07D 317/46; C07D 333/60; C07D 401/04; C07D 403/04; C07D 405/04; C07D 405/14; C07D 409/04; C07D 471/04
See application file for complete search history.

(56) References Cited

PUBLICATIONS

Dumbre, et al., Suzuki-Miyaura Cross-coupling Reaction between Aryl Halides and Phenylboronic Acids over Gold Nano-particles Supported on MgO (or CaO) and Other Metal Oxides, J. of Catalysis, 301, 134-140 (2013).*

(Continued)

*Primary Examiner* — Erich A Leeser
(74) *Attorney, Agent, or Firm* — Sam L. Nguyen; Hamilton DeSanctis + Cha, LLP

(57) ABSTRACT

In one embodiment, the present application discloses a catalyst composition comprising: a) a reaction solvent or a reaction medium; b) organometallic nanoparticles comprising: i) a nanoparticle (NP) catalyst, prepared by a reduction of an iron salt in an organic solvent, wherein the catalyst comprises at least one other metal selected from the group consisting of Pd, Pt, Au, Ni, Co, Cu, Mn, Rh, Ir, Ru and Os or mixtures thereof; c) a ligand; and d) a surfactant; wherein the metal or mixtures thereof is present in less than or equal to 50,000 ppm relative to the iron salt.

9 Claims, 6 Drawing Sheets

Related U.S. Application Data

(60) Provisional application No. 62/163,466, filed on May 19, 2015, provisional application No. 62/201,849, filed on Aug. 6, 2015.

(51) Int. Cl.

| | | |
|---|---|---|
| *C07D 333/60* | (2006.01) |
| *C07D 317/46* | (2006.01) |
| *C07D 317/22* | (2006.01) |
| *C07D 241/18* | (2006.01) |
| *C07D 211/70* | (2006.01) |
| *C07D 213/30* | (2006.01) |
| *C07D 213/64* | (2006.01) |
| *C07D 215/06* | (2006.01) |
| *C07D 239/26* | (2006.01) |
| *C07D 239/54* | (2006.01) |
| *C07D 403/04* | (2006.01) |
| *C07D 405/14* | (2006.01) |
| *C07D 409/04* | (2006.01) |
| *C07D 471/04* | (2006.01) |
| *C07C 209/32* | (2006.01) |
| *C07C 211/45* | (2006.01) |
| *C07C 201/12* | (2006.01) |
| *C07C 205/12* | (2006.01) |
| *C07C 269/06* | (2006.01) |
| *C07C 209/68* | (2006.01) |

(56) References Cited

PUBLICATIONS

B.H. Lipshutz et al., Palladium Nanoparticle-Nanomicelle Combination . . . , Ang. Chem. Int. Ed. 2014, 53, 14051-14054.

B.H. Lipshutz et al., TPGS-750-M: A Second Generation Amphiphile . . . , J. Org. Chem, 2011, 76, 4379-4391.

J.G.C. Veinot et al., Iron/Iron Oxide Nanoparticles: A Versatile Support for Catalytic Metals . . . , Chem. Comm., 2010, 46, 2411-2413.

B.H. Lipshutz et al., Sustainable Fe-ppm Pd Nanoparticle Catalysis of Suzuki-Miyaura . . . , Science, Research Report, Sep. 4, 2015, vol. 349, Issue 6252, 1087.

B.H. Lipshutz et al., Transition-Metal-Catalyzed Cross-Couplings Going Green: in Water at Room Temperature, Aldrichimica Acta, vol. 41, No. 3, 2008.

B.H. Lipshutz, Organic Letters, vol. 10, No. 7 (2008), pp. 1333-1336.

B.H. Lipshutz, Organic Letters, vol. 10, No. 7 (2008), pp. 1325-1332.

Smith, AAPS Journal, vol. 5, No. S1 (2003) Available at http://www.aapsj.org/abstract/Am_2003/AAPS2003-000558.pdf.

Maskill, Howard, The investigation of Organic Reactions and Their Mechanisms, Blackwell Publishing, 2006, 63-64.

\* cited by examiner

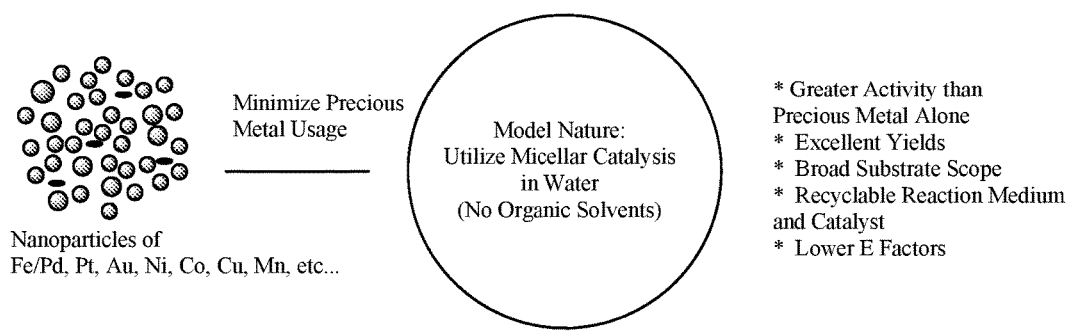
Figure 1: Approach to Suzuki-Miyaura Coupling Reactions

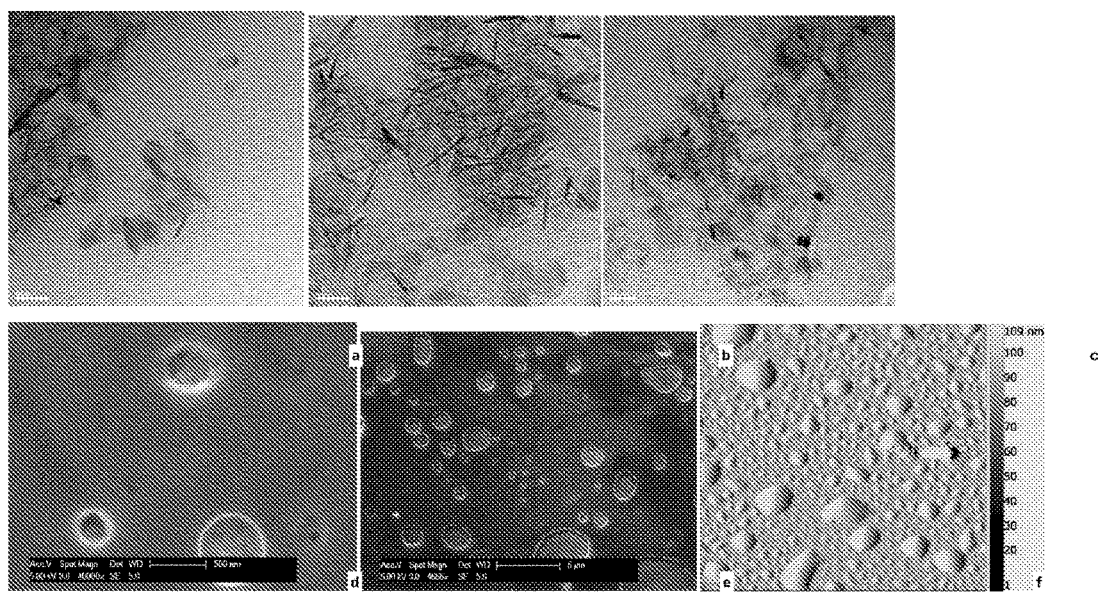
Figure 2. Cryo-TEM analysis of Fe/Pd nanorods in aqueous TPGS-750-M (a-c); SEM of solid nanomaterial (d-e); AFM image of solid nanomaterial (f). See SI for details.

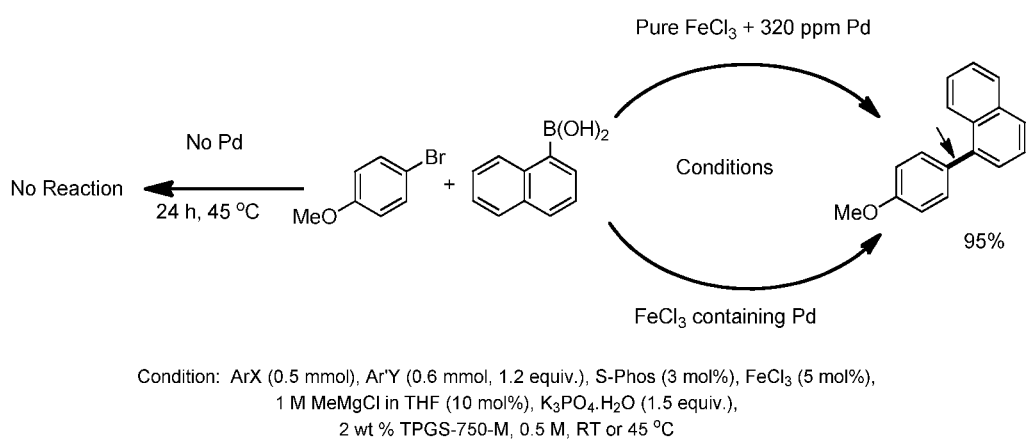
Figure 3. Results using doped and non-doped iron nanoparticles.

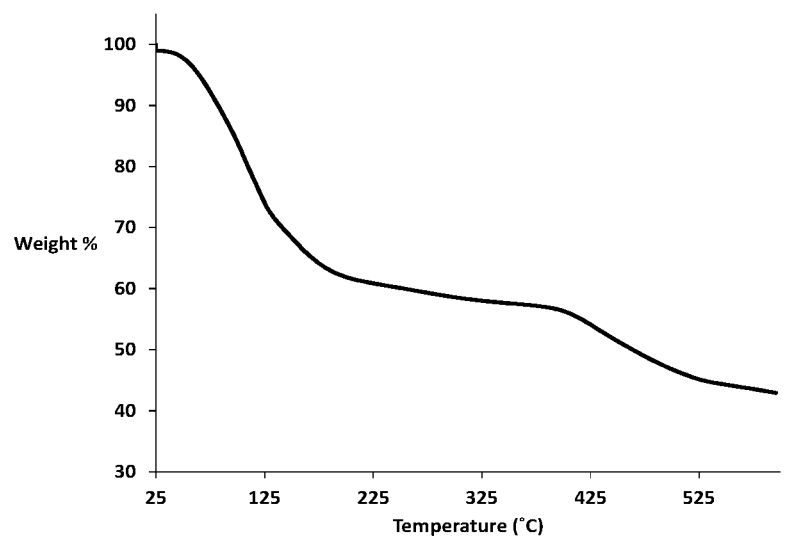
Figure 4. TGA analysis of Fe/Pd nanomaterial.

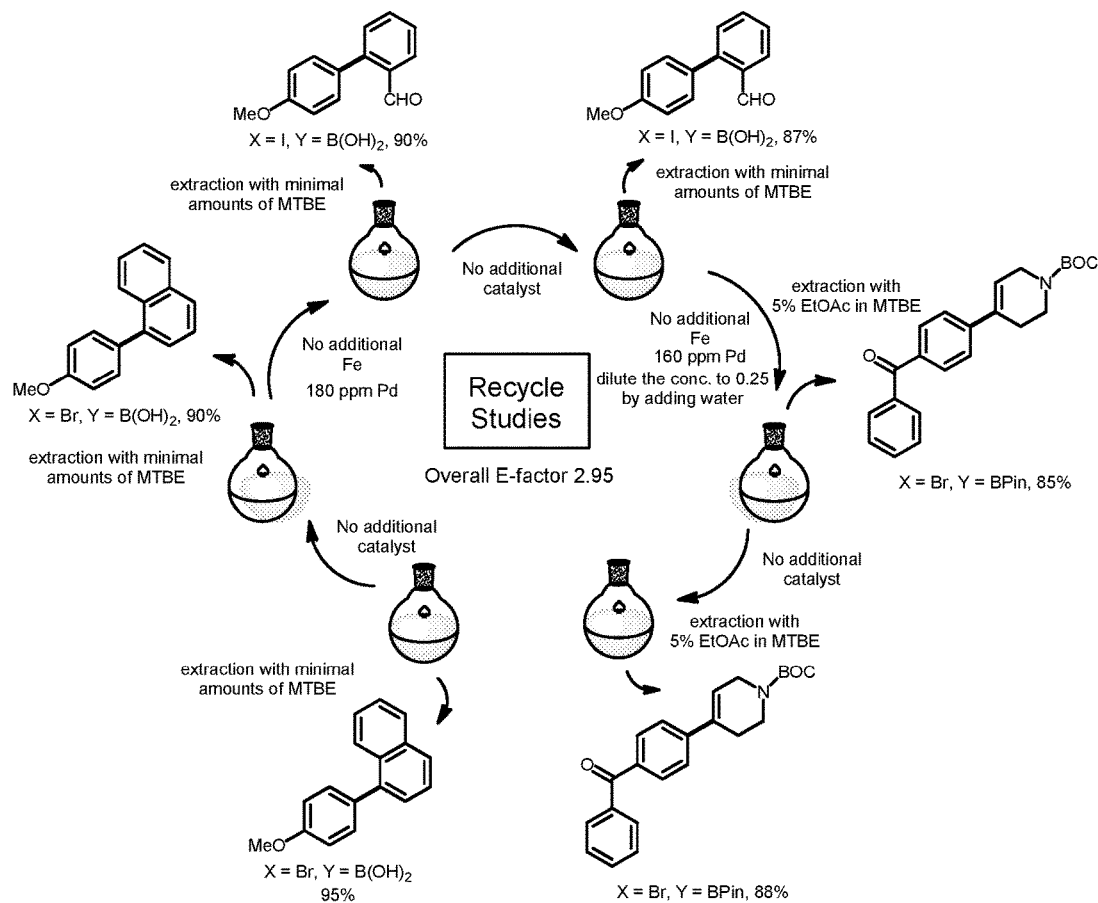
Figure 5. Recycling of the aqueous reaction mixture.

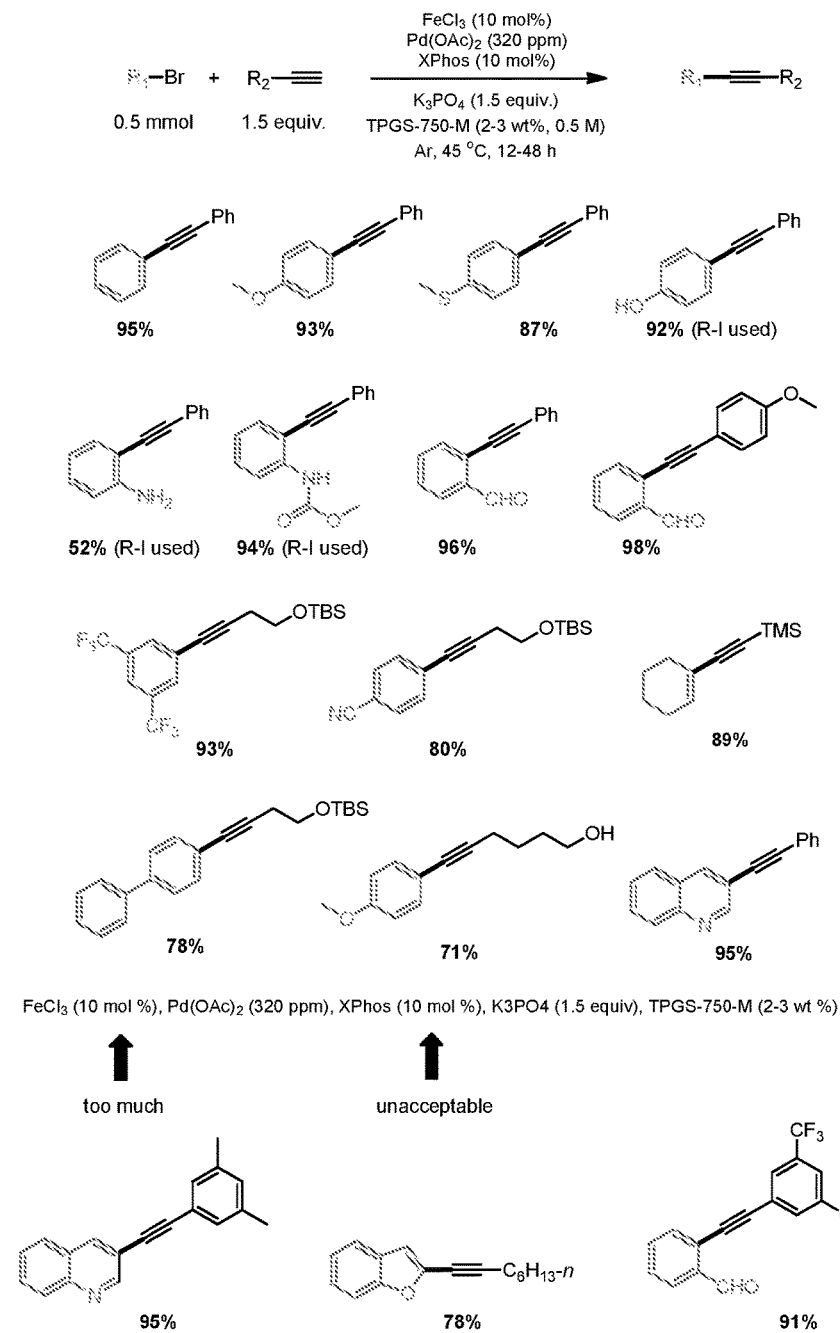
Figure 6: Results of Sonogashira Coupling Reactions

US 10,189,016 B2

NANO-TO-NANO FE/PPM PD CATALYSIS OF CROSS-COUPLING REACTIONS IN WATER

RELATED APPLICATION

This application claims the benefit of U.S. Provisional Application No. 62/163,466 filed May 19, 2015 and U.S. Provisional Application No. 62/201,849 filed Aug. 6, 2015, which are incorporated herein by reference.

BACKGROUND OF THE INVENTION

Precious metal catalysis in organic synthesis, in large measure, has been and continues to be among the most heavily utilized inroads to C—C, C—H and C-heteroatom bond constructions. Chief among these lies palladium chemistry, and with the 2010 Nobel Prizes recognizing Pd-catalyzed Suzuki, Heck and Negishi couplings, even greater use of these and related processes are to be expected.[1] On the other hand, platinoids, in general, are now regarded as "endangered"; that is, the amount of such metals to which there is economical access is finite, and supplies continue to dwindle. Thus, in a sense, award-winning organopalladium chemistry might be viewed as at odds with sustainability. In one aspect, the coupling reactions utilizes micellar catalysis in water and require no organic solvents.

To circumvent this situation, alternative metals have been studied, in particular nickel[2] and copper,[3] especially as applied to the most heavily used Pd-catalyzed cross-coupling: Suzuki-Miyaura reactions.[2a,2e,4] While these have led to varying degrees of success, in the final analysis, Pd remains, by far, the metal of choice. Ideally, technology that accomplishes the desired transformations would do so at the ppm level of palladium. Furthermore, utilization of trace levels of this metal, perhaps as found as an "impurity" in other inexpensive metal salts, would ultimately translate into both a recycling of natural sources of Pd while the cost for its use, therefore, approaches zero.

SUMMARY OF THE INVENTION

The present application discloses a technology that takes a readily available, earth-abundant iron salt that contains only parts per million (ppm) levels of Pd, and easily processes it into a very active catalyst capable of mediating cross-coupling reactions, such as Suzuki-Miyaura cross coupling reactions, that may be performed in water as the reaction medium, or water as the only reaction medium.

The following embodiments, aspects and variations thereof are exemplary and illustrative are not intended to be limiting in scope.

In one embodiment, there is provided a catalyst composition comprising: a) a reaction solvent or a reaction medium; b) organometallic nanoparticles comprising: i) a nanoparticle (NP) catalyst, prepared by a reduction of an iron salt in an organic solvent, wherein the catalyst comprises at least one other metal selected from the group consisting of Pd, Pt, Au, Ni, Co, Cu, Mn, Rh, Ir, Ru and Os or mixtures thereof; c) a ligand; and d) a surfactant; wherein the metal or mixtures thereof is present in less than or equal to 50,000 ppm relative to the iron salt; or relative to the substrate.

In one variation of the above catalyst composition, the metal or mixtures thereof is present in less than or equal to 40,000 ppm, 30,000 ppm. 20,000 ppm, 10,000 ppm, 5,000 ppm, 3,000 ppm, 2,000 ppm or 1,000 ppm. In another variation, the metal or mixtures thereof is present in less than or equal to 1,000 ppm. In another variation of the composition, the surfactant provides nanomicelles for housing a substrate. In another variation, the polar solvent or polar reaction medium is water. In yet another variation, the polar solvent or polar reaction medium is a glycol or glycol ether selected from ethyleneglycol, propylene glycol, 2-methoxyethanol, 2-ethoxyethanol, 2-propoxyethanol, 2-isopropoxyethanol, 2-butoxyethanol, 2-phenoxyethanol, 2-benzyloxyethanol, 2-(2-methoxyethoxy)ethanol, 2-(2-ethoxyethoxy) ethanol, 2-(2-butoxyethoxy)ethanol, dimethoxyethane, diethoxyethane and dibutoxyethane. In one variation of the above, the organometallic nanoparticles are present as a complex. In another variation, the reaction medium is a micellar medium or an aqueous micellar medium. In another variation, the catalyst composition further comprises water.

In another embodiment, there is provided an aqueous micellar composition for enabling cross-coupling reactions containing organometallic nanoparticles (NPs) as catalyst, comprising: a) an element selected from the group consisting of Fe, C, H, O, Mg, and a halide, or the entire combination thereof; and b) palladium, or at least one other metal selected from the group consisting of Pt, Au, Ni, Co, Cu and Mn, or a mixture thereof; wherein the catalyst (NPs) is prepared from a reduction of an iron salt in a solvent and in the presence of a ligand using a reducing agent.

In one variation, there is provided an aqueous micellar composition for enabling cross-coupling reactions containing organometallic nanoparticles (NPs) as catalyst, comprising: a) an element selected from the group consisting of Fe, C, H, O, Mg, and a halide; and b) palladium, or at least one other metal selected from the group consisting of Pt, Au, Ni, Co, Cu, Mn, Rh, Ir, Ru and Os or a mixture thereof; wherein the catalyst (NPs) is prepared from a reduction of an iron salt in a solvent and in the presence of a ligand using a reducing agent, after which the solvent is removed and to which is then added an aqueous solution containing nanomicelles, wherein the palladium is present in less than or equal to 1,000 ppm of the iron metal complex, and wherein the ligand is present in an amount, on a mole-to-mole basis, comparable to the levels of iron salt being used.

DETAILED DESCRIPTION OF THE INVENTION

In one embodiment, the application discloses a catalyst composition comprising an aqueous micellar medium together with organometallic nanoparticles as a complex, comprising: a) a surfactant, providing nanomicelles for housing a substrate; b) a nanoparticle (NP) catalyst, prepared by a reduction of an iron salt, wherein the catalyst comprises at least one other metal selected from the group consisting of Pd, Pt, Au, Ni, Co, Cu, Mn, Rh, Ir, Ru and Os or a mixture thereof; c) a ligand; and d) water; wherein the metal or a mixture thereof is present in less than or equal to 1,000 ppm of the iron catalyst.

In one variation of the catalyst composition, the nanomicelles house, enclose, encase or surround one or more substrates for a catalytic reaction as described herein. In one variation, the 1,000 ppm is based on a mole to mole basis. In one variation, the relative ppm is determined on a wt/wt basis. In another variation, the other metal is selected from Pd, Pt and Ni, or a mixture thereof.

In another embodiment, there is provided an aqueous micellar composition for enabling cross-coupling reactions containing organometallic nanoparticles (NPs) as catalyst, comprising: a) an element selected from the group consisting of Fe, C, H, O, Mg, and a halide; and b) palladium, or at least one other metal selected from the group consisting of Pt, Au, Ni, Co, Cu, Mn, Rh, Ir, Ru and Os, or a mixture thereof; wherein the catalyst (NPs) is prepared from a reduction of an iron salt in a solvent and in the presence of a ligand using a reducing agent, after which the solvent is removed and to which is then added an aqueous solution containing nanomicelles, wherein the palladium is present in less than or equal to 1,000 ppm of the iron metal complex, and wherein the ligand is present in an amount, on a mole-to-mole basis, comparable to the levels of iron salt being used, or the levels of the substrate being used.

In one aspect of the above composition, the iron is selected from the group consisting of a Fe(II) or Fe(III) salt, or a Fe(II) salt precursor or Fe(III) salt precursor. In one variation of the composition, the catalyst comprising at least one other metal selected from the group consisting of Pd, Pt, Au, Ni, Co, Cu, Mn, Rh, Ir, Ru and Os is naturally present in the iron salt in amounts less than or equal to 1 ppm, 10 ppm, 50 ppm, 100 ppm, 200 ppm, 300 ppm, 400 ppm or 500 ppm relative to the iron complex. In another variation, the iron salt is highly purified iron, such as with an assay as >99.99% trace metal basis, or having less than 0.01% other metals, and the catalyst is added to the composition to be present in the iron salt in an amount that is less than or equal to 1 ppm, 10 ppm, 50 ppm, 100 ppm, 200 ppm, 300 ppm, 400 ppm or 500 ppm relative to or within the iron complex, or the iron salt. In another variation, the catalyst is added prior to reduction and NP formation.

In one variation of the catalyst composition and the method disclosed in the present application, the reaction solvent is water. In another variation, the reaction solvent is a mixture of water and an organic solvent or co-solvent. In one variation, the composition comprises water in an amount of at least 1% wt/wt of the mixtures. In another embodiment, the water in the mixture is present in an amount of at least 5%, at least 10%, at least 50%, at least 75%, at least 90% or at least 99% wt/wt or more of the mixture. In another variation, the organic co-solvent in the reaction solvent is present in at least 5%, 7%, 10%, 15%, 20%, 30%, 40%, 50%, 70%, 80% or 90% with the remaining being water or a polar solvent. In yet another variation, the organic co-solvent is present at a wt of organic co-solvent to the wt of water (wt/wt) of 1/10, 2/10, 3/10, 5/10, 7/10, 9/10, 10/10, 12/10, 15/10, 17/10, 20/10, 25/10, 30/10, 35/10, 50/10, 60/10, 70/10, 80/10, 90/10, 100/10, 150/10, 200/10, 250/10, 300/10, 400/10, 500/10, 600/10, 700/10, 800/10, 900/10, 1,000/10, 5,000/10 and 10,000/10. In one variation, the reaction may be performed in one of the above reaction solvent composition by wt/wt (e.g., 1/10), as a first solvent composition, and when the reaction is completed, the reaction solvent composition may be changed to another composition or second wt/wt composition (e.g., 150/10), to facilitate at least one of the processing of the reaction mixture; transferring of reaction mixture, isolating components of the reaction mixture including the product, minimizing the formation of emulsions or oiling out of the reactants and/or products, and providing an increase in the reaction yields; or a combination thereof. Depending on the reaction or processing steps, the reaction mixture may be changed to a third or other, subsequent solvent composition. In another aspect, water is the only reaction medium in the mixture. In another aspect, non-exclusive examples of the organic solvent or co-solvent may include $C_1$-$C_6$ alcohols such as methanol, ethanol, propanol, isopropanol, butanol(s), n-butanol, 2-butanol, etc . . . , hydrocarbons such as cyclohexane, heptane(s), hexanes, pentanes, isooctane, and toluene or xylenes, or acetone, amyl acetate, isopropyl acetate, ethyl acetate, methyl acetate, methyl formate, diethyl ether, cyclopropyl methyl ether, THF, 2-methyl-THF, acetonitrile, formic acid, acetic acid, ethyleneglycol or PEGs/MPEGs of any length of ethylenoxy units, trifluoromethylbenzene, triethylamine, dioxane, sulfolane, MIBK, MEK, MTBE, DMSO, DMF, DMA, NMP or mixtures thereof.

In one variation of the above, there is provided a composition, such as the catalyst composition, prepared by the above described process. In one variation of the above composition, the halide is Cl or Br. In another variation, the other metal may be present in any of their oxidation states, including 1, 2, 3, 4 or 5. In one aspect of the above composition, the reducing agent is a Grignard reagent. In one variation of the composition, the reduction of the iron salt is performed in an ether solvent. In one variation, the ether solvent is selected from the group consisting of methyl ether, ethyl ether, THF, Me-THF, dioxane, mono-glyme and di-glyme. In one variation of the composition, the solvent is selected from the group consisting of THF, Methyl-THF, toluene, i-PrOAc, MTBE and mixtures thereof. In another variation, the reduction is performed at a temperature between −25° C. and 25° C. In one aspect, the ligand is present in about a 1:1; 1:1.1; 1:1.2; 1:1.3; 1:1.4 or 1:1.5; or 1.5:1; 1.4:1; 1.3:1; 1.2:1; 1.1:1 on a mole-to-mole basis to the levels of iron salt being used. In one embodiment, there is provided a composition prepared by the above method.

In another aspect of the above composition, the iron is selected from the group consisting of a Fe(II) or Fe(III) salt as precursor to the catalyst. In another aspect of the composition, the palladium is naturally present in the iron salt in amounts less than or equal to 500 ppm relative to the iron complex.

In one variation of the composition, the Pt, Au, Ni, Co, Cu, Mn, Rh, Ir, Ru and Os or a mixture thereof is naturally present in less than or equal to 500 ppm (0.05 mole %) within the iron salt. In another variation of the composition, the Pt, Au, Ni, Co, Cu, Mn, Rh, Ir, Ru and Os or a mixture thereof is added to the composition in less than or equal to 1,000 or 500 ppm within the iron salt.

In another aspect, the amount of Pd present is controlled by external addition of a Pd salt to an iron salt prior to reduction and NP formation. In one variation of the composition, the iron is a purified iron salt, such as a highly purified iron salt, such as $FeCl_3$ or a highly purified $FeCl_3$. In another variation, the iron salt, such as $FeCl_3$, has an assay of >99.99% trace metal basis, or less than 0.01% other metals. In another variation, the iron salt is purified with substantially no palladium. In one variation of the composition, the amount of Pd present by external addition of a Pd salt may be about 1-50,000 ppm, 1-1,000 ppm, 1-500 ppm, 1-300 ppm or 1-200 ppm; 100 ppm, 200 ppm, 300 ppm, 500 ppm or 1000 ppm or more.

In another aspect of the composition, the reducing reagent is a Grignard reagent selected from the group consisting of MeMgCl, MeMgBr, MeMgI, EtMgCl, EtMgBr, EtMgI, i-PrMgCl, i-PrMgBr, i-PrMgI, PhMgCl, PhMgBr, PhMgI, n-hexyl-MgBr, n-hexyl-MgCl, n-hexyl-MgBr, n-hexyl-MgCl, n-hexyl-MgI, $NaBH_4$, $liBH_4$, $BH_3$-THF, $BH_3$—$SMe_2$, borane, DIBAL-H and $LiAlH_4$; and mixtures thereof. In one variation of the composition, the Grignard reagent is in an ethereal solvent. In another variation, the solvent is THF.

In another aspect, the surfactant is selected from the group consisting of TPGS-500, TPGS-500-M, TPGS-750, TPGS-750-M, TPGS-1000 and TPGS-1000-M, Nok and PTS. In one variation of the composition, the surfactant is selected from the group consisting of Poloxamer 188, Polysorbate 80, Polysorbate 20, Solutol HS 15, PEG-40 Hydrogenated castor oil (Cremophor RH40), PEG-35 Castor oil (Cremophor EL), PEG-8-glyceryl capylate/caprate (Labrasol), PEG-32-glyceryl laurate (Gelucire 44/14), PEG-32-glyceryl palmitostearate (Gelucire 50/13); Polysorbate 85, Polyglyceryl-6-dioleate (Caprol MPGO), Sorbitan monooleate (Span 80), Capmul MCM, Maisine 35-1, Glyceryl monooleate, Glyceryl monolinoleate, PEG-6-glyceryl oleate (Labrafil M 1944 CS), PEG-6-glyceryl linoleate (Labrafil M 2125 CS), Propylene glycol monocaprylate (e.g. Capmul PG-8 or Capryol 90), Propylene glycol monolaurate (e.g., Capmul PG-12 or Lauroglycol 90), Polyglyceryl-3 dioleate (Plurol Oleique CC497), Polyglyceryl-3 diisostearate (Plurol Diisostearique) and Lecithin, or mixtures thereof. In another variation, the surfactant is selected from the group consisting of Solutol HS 15, PEG-40 Hydrogenated castor oil (Cremophor RH40), PEG-35 Castor oil (Cremophor EL), Polysorbate 85, or mixtures thereof. In another variation, the surfactant is present as a 0.1 to 20 weight % in water, 1 to 5 weight % in water, or 2 weight % in water. In another aspect, the composition further comprises an organic solvent.

In another aspect, the composition further comprises a ligand, such as a mono- or bi-dentate phosphine or NHC ligand selected from the group consisting of PPh$_3$, (o-Tol)$_3$P, (p-Tol)$_3$P, dppf, dtbpf, BiDime, Tangphos, IMes, IPr, SPhos, t-BuSPhos, XPhos, t-BuXPhos, BrettPhos and t-Bu-BrettPhos, and HandaPhos or an analog thereof. In another aspect of the composition, the iron metal complex as nanoparticles is heterogeneous and can be isolated from the composition, stored and recycled and re-use.

In another embodiment, there is provided a method for performing a cross coupling reaction between a first coupling substrate of the formula I with a second coupling substrate of the formula II in a reaction condition sufficient to form the coupled product of the formula III:

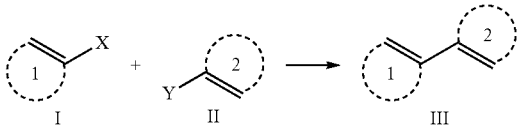

wherein: X is selected from the group consisting of Cl, Br and I; Y is selected from the group consisting of B(OH)$_2$, B(OR)$_2$, cyclic boronates, acyclic boronates, B(MIDA), Bpin and BF$_3$K, where R is selected from methyl, ethyl, propyl, butyl, isopropyl, ethylene glycol, trimethylene glycol and pinacol;
each of the groups

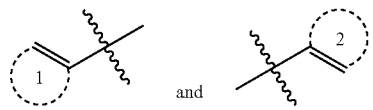

is independently selected from the group consisting of an alkene or a substituted alkene, a cycloalkene or a substituted cycloalkene, an alkyne or a substituted alkyne, an aryl or a substituted aryl, and a heteroaryl or a substituted heteroaryl; the method comprising: i) forming a micelle composition comprising aqueous nanoparticles in which the partners I and II are solubilized in water, and an organometallic complex comprising: a) iron nanoparticles, wherein another metal is present in less than 50,000 ppm, or less than 1,000 ppm; b) other metal nanoparticles admixed with iron nanoparticles; and ii) contacting the first coupling substrate with the second coupling substrate in water under a condition sufficient to form a product mixture comprising a cross coupling product of the formula III.

In another embodiment, there is provided a method for performing a cross coupling reaction between a first coupling substrate of the formula I with a second coupling substrate of the formula II in a reaction condition sufficient to form the coupled product of the formula III:

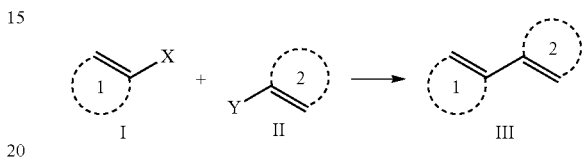

wherein: X is selected from the group consisting of Cl, Br and I, and pseudo halides; Y is selected from the group consisting of B(OH)$_2$, B(OR)$_2$, cyclic boronates, acyclic boronates, B(MIDA), Bpin and BF$_3$K, where R is selected from methyl, ethyl, propyl, butyl, isopropyl, ethylene glycol, trimethylene glycol and pinacol;
each of the groups

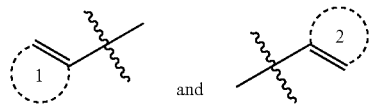

is independently selected from the group consisting of an alkene or a substituted alkene, a cycloalkene or a substituted cycloalkene, an alkyne or a substituted alkyne, an aryl or a substituted aryl, and a heteroaryl or a substituted heteroaryl; the method comprising: i) forming a micelle composition comprising aqueous nanoparticles in which the partners I and II are solubilized in water, and an organometallic complex comprising iron nanoparticles, wherein another metal is present in less than 50,000 ppm relative to the limiting substrate of the formula I or formula II; and ii) contacting the first coupling substrate with the second coupling substrate in water under a condition sufficient to form a product mixture comprising a cross coupling product of the formula III. In one variation of the method, the metal or mixtures thereof is present in less than or equal to 40,000 ppm, 30,000 ppm, 20,000 ppm, 10,000 ppm, 5,000 ppm, 3,000 ppm, 2,000 ppm or 1,000 ppm.

In one variation of the above method, the other metal (i.e., the "another metal" that is other than iron cited above) is palladium. In another variation, the other metal is present in less than 700 ppm, 500 ppm or 300 ppm. In one variation of the method, the micelle composition is a catalyst composition comprising an aqueous micellar medium together with organometallic nanoparticles as a complex, comprising: a) a surfactant, providing nanomicelles for housing a substrate; b) a nanoparticle (NP) catalyst, prepared by a reduction of an iron salt, wherein the catalyst comprises at least one other metal selected from the group consisting of Pd, Pt, Au, Ni, Co, Cu, Mn, Rh, Ir, Ru and Os or a mixture thereof; c) a ligand; and d) water; wherein the metal or a mixture thereof is present in less than or equal to 50,000 ppm or 1,000 ppm relative to the substrate. In another variation of the method, the coupling reaction is performed between room temperature, or about 20° C. and 50° C.

In another aspect of the above method, the metal, other than Pd, is selected from the group consisting of Pt, Au, Ni, Co, Cu, Mn, Rh, Ir, Ru and Os or a mixture thereof. In another aspect, the method further comprises: iii) contacting the product mixture with an organic solvent to form an organic phase and an aqueous phase; and iv) separating the organic phase from the aqueous phase containing the micelle composition as well as the iron/ppm Pd nanoparticles.

In another aspect, the method further comprising: v) re-cycling the aqueous phase containing the micelle composition and Fe/ppm Pd nanoparticles for use in a subsequent cross coupling reaction. In another aspect of the method, the source of iron is selected from $FeCl_3$, impure $FeCl_3$ and mixtures thereof, and the reducing agent is a Grignard reagent. Impure $FeCl_3$ include 96%, 97%, 98%, 99%, 99% or >99% purity. In another aspect of the method, the reaction condition is a Suzuki-Miyaura coupling condition or a Sonogashira coupling condition, or other common Pd-catalyzed cross-coupling reactions. In one variation of the above, the reaction is an amination reaction, Stille couplings, Negishi couplings, Hiyama couplings and cross-couplings involving oxygen nucleophiles. In another aspect of the method, the reaction is performed at room temperature. In one variation of the above, the reaction is performed at about 20 to 65° C., 20 to 45° C., or 15 to 35° C.

In yet another aspect of each of the above, the method further comprises removal of the solvent in vacuo, and further isolating the nanoparticles from the reaction mixture for re-use or recycling. In another aspect, the method further comprises removal of the solvent in vacuo, and further isolating the nanoparticles from the reaction mixture for re-use or recycling. In one variation, the nanoparticles may be re-use or recycled for 2, 3, 4, 5 or more reactions or processes.

In one variation of the above, the nanoparticles (NPs) are powders. In another variation of the composition, the Pd is present in any of its oxidation states, such as $Pd^o$, Pd(I), Pd(II) or Pd(IV). In one variation, the metal is a trace impurity (e.g., in ppm) in the iron salt. In another variation, the metal is added to the composition comprising the organometallic complex before the addition of the reducing agent.

In one embodiment, the application discloses composites or compositions comprising nanoparticles (NPs) as powders derived from an iron (Fe) metal, such as an Fe(II) salt or an Fe(III) salt. In one aspect, the NPs contain primarily C, H, O, Mg, halogen and Fe in their matrix. In another aspect, these NPs may also contain ppm levels of other metals, especially transition metals (e.g., Pd, Pt, Au, Ni, Co, Cu, Mn, Rh, Ir, Ru and Os, and mixtures thereof), that may be either present in the Fe(II) or Fe(III) salts or the transition metals may be added externally prior to reduction (e.g., using $Pd(OAc)_2$, etc.). In one variation, the transition metal is Pd, Pt or Ni, or a mixture thereof. In the resulting composite, these NPs may be used as heterogeneous catalysts, in an aqueous micellar medium. In another aspect, the NPs maybe used to mediate transition metal-catalyzed reactions. Such metal-catalyzed reactions may include reactions that are catalyzed by Pd (e.g., Suzuki-Miyaura and Sonogashira couplings, etc.), as well as reductions of selected functional groups (e.g., aryl/heteroaryl nitro groups).

In one variation of the above composition, the nanoparticle organometallic complex consists mainly of iron. In another variation, the nanoparticle organometallic complex comprises of a mixture of metals wherein at least 90% wt/wt, 95% wt/wt, 97% wt/wt, 98% wt/wt, 99% wt/wt, 99.5% wt/wt, 99.8% wt/wt or 99.9% wt/wt of the metal is iron. In one variation of the complex, the other metal present in the mixture is palladium.

In one aspect of the composition, the iron metal is selected from the group consisting of a Fe(II) or Fe(III) salt or salt precursor. In one variation, the iron metal is $FeCl_3$.

In another aspect, the palladium is present in the iron metal complex in amounts less than or equal to 400 ppm relative to the iron metal complex. In one variation, the palladium is $Pd^o$, prepared by reduction of $Pd(OAc)_2$ or other Pd salts. In another variation, the iron metal complex is doped by addition of the palladium, before or after reduction of the iron salt. In another variation of the above composition, the palladium is present in less than about 800 ppm, less than 700 ppm, less than 600 ppm, less than 500 ppm, less than 400 ppm, less than 300 ppm, less than 200 ppm or less than 100 ppm.

In another aspect, the iron metal complex as nanoparticles is heterogeneous and can be isolated, stored and recycled. In one variation of the above composition, the nanoparticle complex may be stored at room temperature for at least 1 month, 2 month, 3 months, 4 months, 5 months or more than 6 months without any noticeable degradation.

In one variation, the compound of the formula I and the compound of the formula II may also include any sp2-sp2 combination, including cyclopropyl arrays. In one aspect of the above, the metal is Pd, Pt or Ni, or mixtures thereof. In another variation of the above, the iron metal complex containing palladium metal as nanoparticles is present at less than about 10 mol percent (mol %), 8 mol percent, 6 mol percent, 5 mol percent, 3 mol percent, 2 mol percent or less than about 1 mole percent relative to the first coupling substrate of the formula I or the second coupling substrate of the formula II.

In another variation of the above, the substituent is 1, 2 or 3 substituents selected from the group consisting of —$OCH_3$, —$CF_3$, —$NR^1R^2$, —$CH(OC_{1-6}$ alkyl$)_2$, —$C(O)NR^1R^2$, —CHO, —$CO_2C_{1-12}$ alkyl, —$CO_2C_{6-12}$ aryl, —$CO_2C_{3-10}$ heteroaryl, —$C(O)C_{6-12}$ aryl, —$C(O)C_{3-10}$heteroaryl, wherein each $R^1$ and $R^2$ is independently selected from H and $C_{1-6}$ alkyl.

In another aspect of the above, the method further comprises: iii) contacting the product mixture with an organic solvent to form an organic phase and an aqueous phase; iv)

separating the organic phase from the aqueous phase containing the micelle composition as well as the iron/ppm Pd nanoparticles.

In another aspect of the above, the method further comprises v) re-cycling the aqueous phase containing the micelle composition and Fe/ppm Pd nanoparticles for use in a subsequent cross coupling or other reactions. In another aspect of the above method, the source of iron is selected from $FeCl_3$, impure $FeCl_3$ and mixtures thereof. In another aspect, the reducing agent is a Grignard reagent. In one variation of the above, there is provided a catalyst composition prepared by the above described process.

This technological advance is based on the confluence of several reaction variables: The choice and source of the iron salt, the method for its conversion to nanoparticles, and the use of micellar catalysis conditions. In one aspect, the treatment of $FeCl_3$ or impure $FeCl_3$ with an equivalent of MeMgCl in a minimal amount of a solvent, such as an ether, such as THF, at room temperature affords nanoparticles that, after solvent removal in vacuo, can be used directly in a cross coupling reaction. Alternatively, these particles may be isolated, such as by filtration, and stored at room temperature for months without any noticeable degradation.

EXPERIMENTAL

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Analysis of a commercially available source[11] of $FeCl_3$ by atomic absorption-ICP led to the finding that approximately 300-350 ppm Pd are present. In some aspects, the sources of $FeCl_3$ that analyzed for less of this metal content [11b] led to incomplete reactions under otherwise identical conditions. Attempts to use ppm levels of Pd in the absence of pre-formed iron-based nanoparticles led to virtually no reaction, suggesting that release of palladium into the aqueous medium is not responsible for the observed catalysis. Doping of highly purified $FeCl_3$ (99.9999%)[11b,12] with 350 ppm $Pd(OAc)_2$, upon reduction with MeMgCl, gave reagent of comparable activity. Doping the $FeCl_3$ with ppm levels of other metals, such as $NiCl_2$, $CoCl_3$, $Cu(OAc)_2$ or $CuBr_2$ led to catalysts that gave variable levels of product formation; in all cases the yields were considerably lower than those obtained in the presence of added $Pd(OAc)_2$ (Table 1).

TABLE 1

Attempts to dope $FeCl_3$ with alternative metals

[Reaction scheme: 4-R-bromobenzene (R = H, OMe, Me) + naphthalen-1-ylboronic acid → biaryl product (15-38%); conditions: $FeCl_3$ (5 mol %), SPhos (3 mol %), Doping metal (500 ppm), MeMgCl (10 mol %), $K_3PO_4$ (1.5 equiv), 2 wt % TPGS-750-M, 45° C., 24 h]

| entry | doped metal | R | % yield |
|---|---|---|---|
| 1. | $NiCl_2$, $Ni(acac)_2$ | H | NR |
| 2. | $NiCl_2$, $Ni(acac)_2$ | OMe | NR |
| 3. | $NiCl_2$, $Ni(acac)_2$ | Me | NR |
| 4. | $CoCl_3$ | H | 15% |
| 5. | $CoCl_3$ | OMe | 18 |
| 6. | $CoCl_3$ | Me | 38 |
| 7. | $MnCl_2$ | H | 5% |
| 8. | $MnCl_2$ | OMe | NR |
| 9. | $MnCl_2$ | Me | NR |
| 10. | $Cu(OAc)_2$, $CuBr_2$ | H | NR |

The nature of the iron salt plays a major role in the activity of the resulting nanoparticles formed, as does the manner in which the salt is reduced. Attempts to use either $Fe(acac)_3$ or iron pyrophosphate ($Fe_4(P_2O_7)_3$) as precursors led to a far less reactive catalyst than that derived from $FeCl_3$. In some aspects, the nature of the reducing agent is also important. While use of i-PrMgCl led to a reagent of comparable activity, both PhMgCl and n-hexyl-MgBr, among other reductants (e.g., $NaBH_4$) afforded nanoparticles that were inferior in a standard Suzuki-Miyaura coupling (Table 2).

TABLE 2

Impact of the reducing agent on the activity of iron nanoparticles

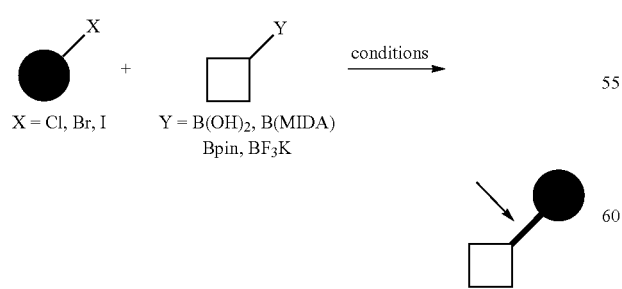

| Reductant (6 mol %) | % 1 |
|---|---|
| NaBH₄ | 28 |
| iPrMgCl | 92 |
| HexMgBr | 75 |
| PMHS | 5 |
| PhMgCl | 76 |
| MeMgCl | 95 |
| MeMgBr | 93 |

In one aspect, only 3 mol percent of these Fe/ppm Pd nanoparticles is needed, to which are added an aqueous solution containing 2 weight percent of a commercially available designer surfactant TPGS-750-M,[5] followed by a base ($K_3PO_4$; 1.5-2.0 equiv; Scheme 1). The choice of ligand was also significant (Scheme 2), with both SPhos[6] and XPhos[7] affording the best results (Scheme 2). Depending upon the reaction partners, vigorous stirring at temperatures between ambient and 45° C. is sufficient to drive couplings to completion. In certain aspects, the reactions are typically complete in the 12-24 hour time frame. In some aspects, the reactions are conducted at a global concentration of 0.5 M.

Condition: ArX (0.5 mmol), Ar'Y (0.6 mmol), S-Phos (3 mol %), FeCl₃ (5 mol %), 1M MeMgBr in THF (10 mol %), K₃PO₄·H₂O (1.5 equiv.), 2 wt % TPGS-750-M, 0.5M, RT or 45° C.

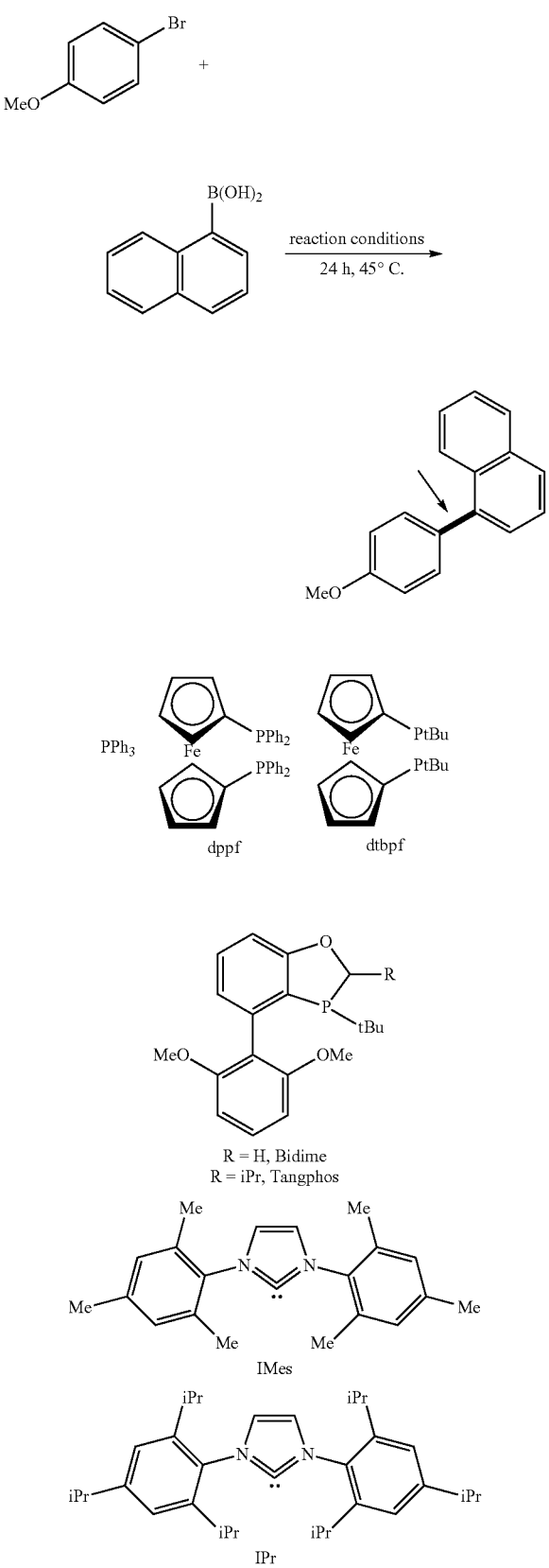

Scheme 1. General reaction scheme for Fe/Pd-catalyzed Suzuki-Miyaura cross-couplings.

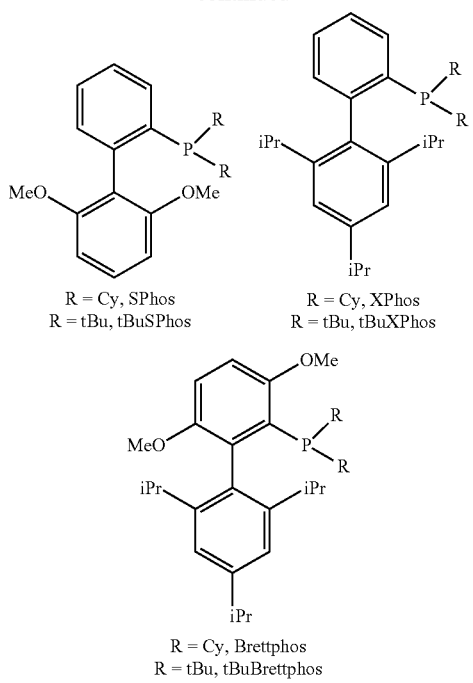

R = Cy, SPhos
R = tBu, tBuSPhos

R = Cy, XPhos
R = tBu, tBuXPhos

R = Cy, Brettphos
R = tBu, tBuBrettphos

Scheme 2. Impact of ligand on the cross-coupling.

| Entry | Ligand | % Yield |
|---|---|---|
| 1 | None | none |
| 2 | PPh3 | 28 |
| 3 | dppf | 70 |
| 4 | dtbpf | 75 |
| 5 | Bidime | 18 |
| 6 | Tangphos | 69 |
| 7 | IMes | 50 |
| 8 | IPr | 70 |
| 9 | SPhos | 98 |
| 10 | tBuSPhos | 92 |
| 11 | XPhos | 94 |
| 12 | tBuXPhos | 89 |
| 13 | BrtettPhos | 44 |
| 14 | tBuBrrettPhos | 40 |

Many representative cases illustrated in Tables 3-5. A broad variety of aromatic and heteroaromatic arrays, with either being the aryl halide or boron-containing source, can be tolerated, as can numerous functional groups dispersed throughout either coupling partner. Thus, functionality such as $CF_3$, amines, acetals, amides, aldehydes, esters, ketones, phosphate esters, nitro groups, polyaromatics, sulfonamides and carbamates are exemplified.

Several types of heteroaromatic units are also amenable, including nitrogen-containing moieties, the products from which might present complications as competing ligands for Pd. Both bromides and iodides are excellent educts, while the nature of the boron species involved can be any of the commonly employed boronic acids, Bpin[8] or MIDA boronates,[9] or $BF_3K$ salts.[10]

TABLE 3

Couplings between aryl halides and aryl boron derivatives

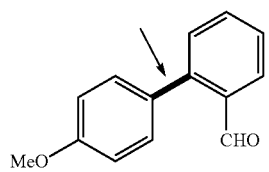

X = Br, Y = B(OH)$_2$, 12 h, 86%
X = I, Y = B(OH)$_2$, 11 h, 91%

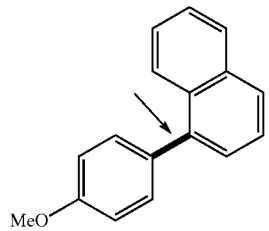

X = Br, Y = B(OH)$_2$, 12 h, 95%
X = Br, Y = B(OH)$_2$, 24 h, 90%, RT
X = Br, Y = B(MIDA), 12 h, 97%

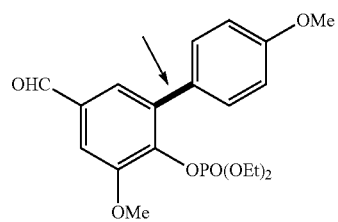

X = I, Y = B(OH)$_2$,
28 h, 95%

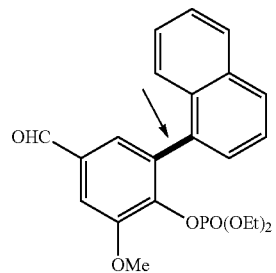

X = I, Y = B(OH)$_2$,
24 h, 88%

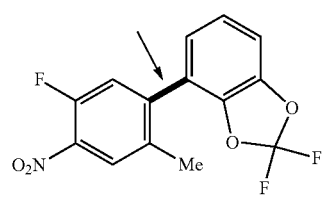

X = Br, Y = B(OH)$_2$
28 h, 81%

TABLE 3-continued
Couplings between aryl halides and aryl boron derivatives
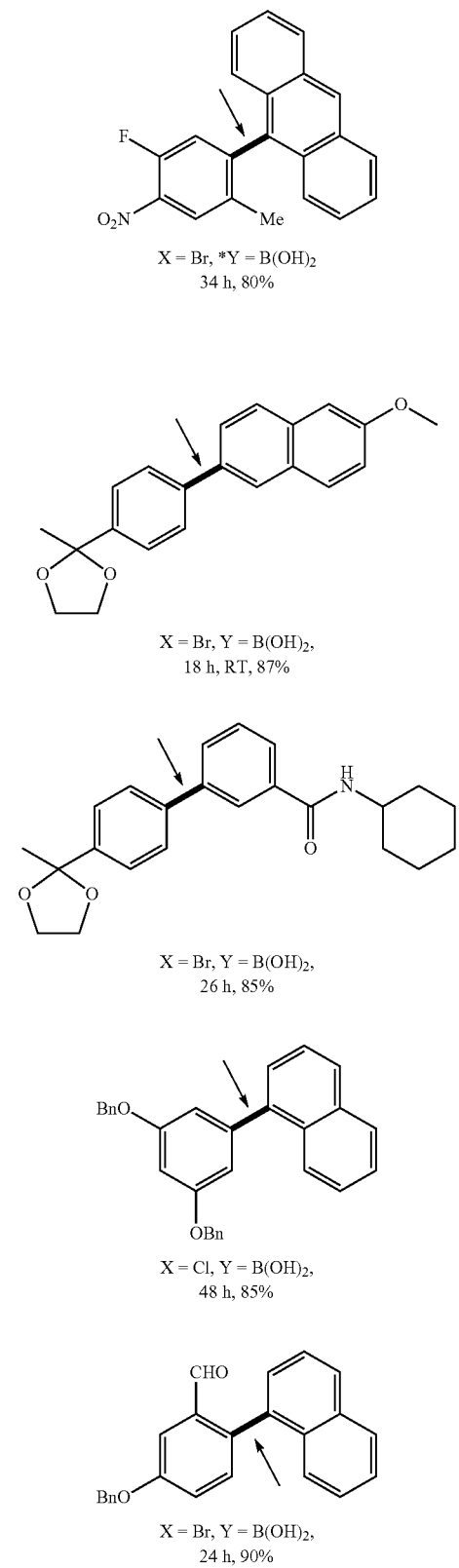
TABLE 4
Suzuki-Miyaura couplings between aryl and heteroaryl partners
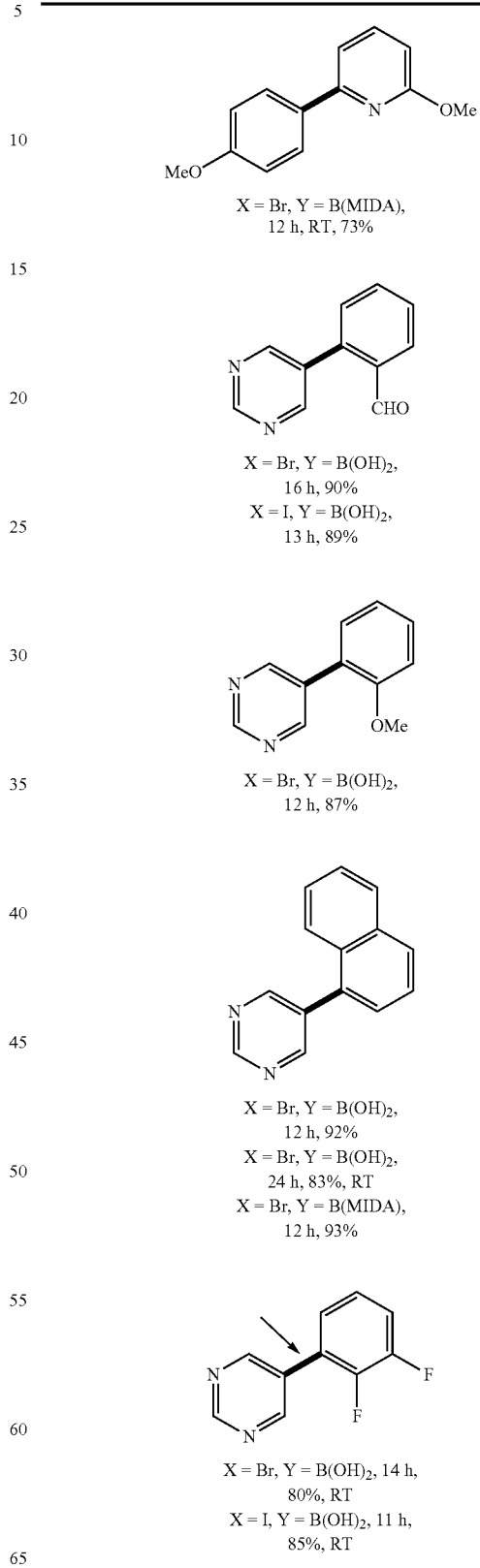

TABLE 4-continued

Suzuki-Miyaura couplings between aryl and heteroaryl partners

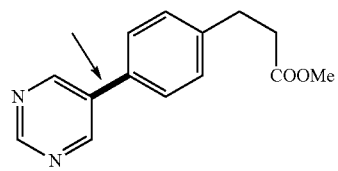

X = Br, Y = B(OH)$_2$,
24 h, 92%

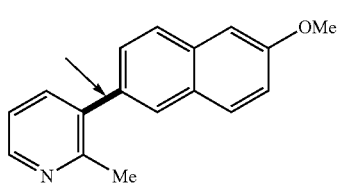

X = Br, Y = B(OH)$_2$,
24 h, 91%

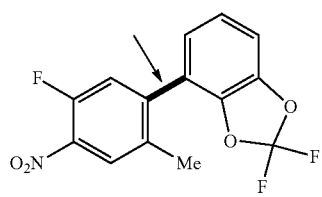

X = Br, Y = B(OH)$_2$,
28 h, 81%

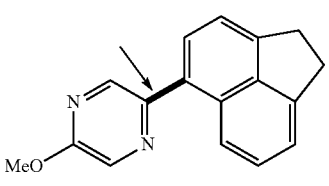

X = Br, Y = B(OH)$_2$,
18 h, 87%

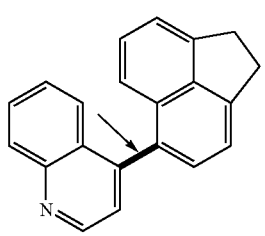

X = Br, Y = B(OH)$_2$,
28 h, 72%

TABLE 4-continued

Suzuki-Miyaura couplings between aryl and heteroaryl partners

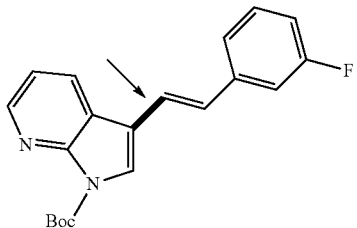

X = Cl, Y = ArBF$_3$K, 48 h, 72%
X = Br, Y = ArBF$_3$K, 42 h, 88%
X = I, Y = ArBF$_3$K, 33 h, 90%
X = I, Y ArB(OH)$_2$, 26 h, 88%

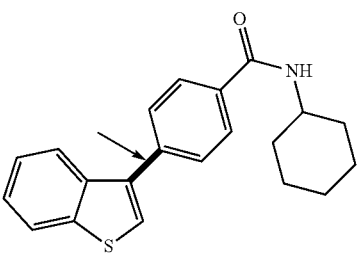

X = Br, Y = B(OH)$_2$,
70 h, 88%

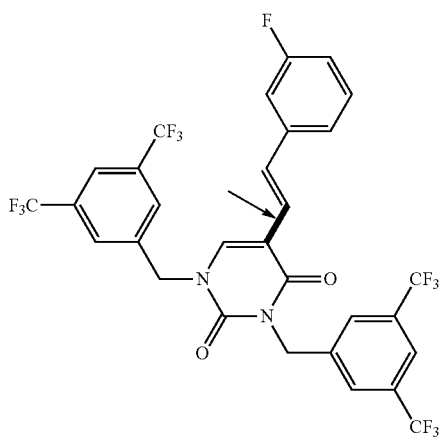

X = Br, Y = BF$_3$K, 24 h, RT, 88%
X = I, Y = BF$_3$K, 20 h, RT, 91%

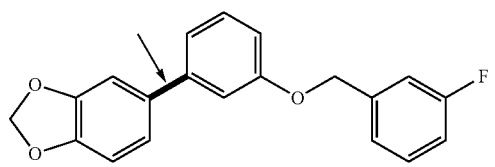

X = Br, Y = B(OH)$_2$,
40 h, 90%

TABLE 4-continued
Suzuki-Miyaura couplings between aryl and heteroaryl partners
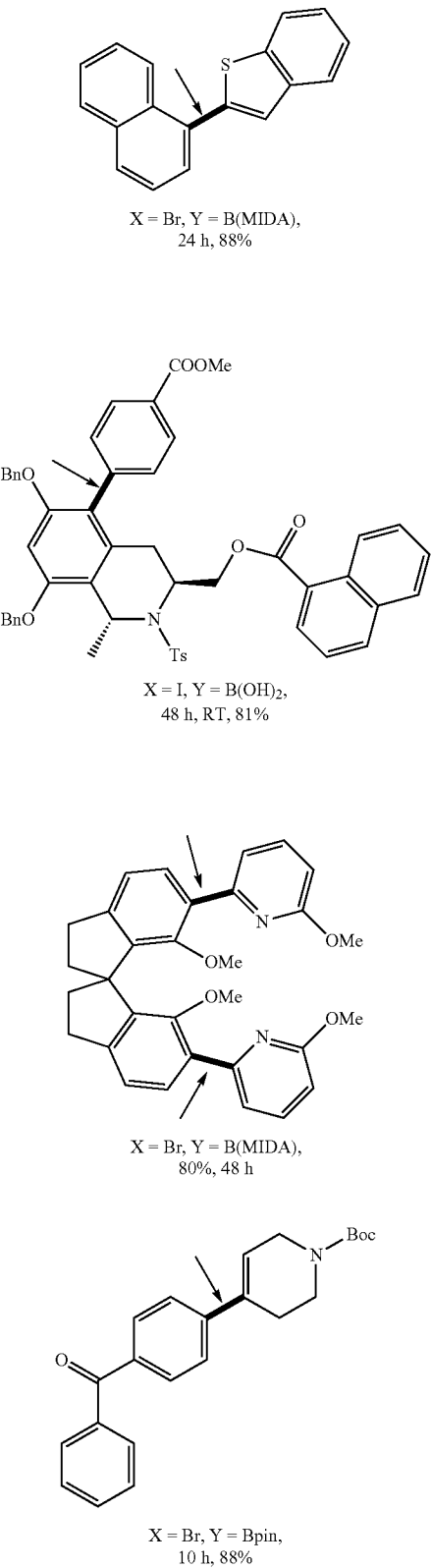
TABLE 5
Suzuki-Miyaura couplings between heteroaryl and heteroaryl partners
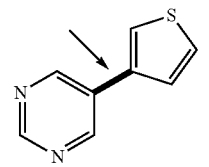
X = Br, Y = B(OH)$_2$,
24 h, 89%, RT
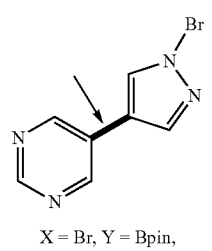
X = Br, Y = Bpin,
24 h, 77%
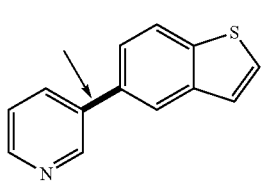
X = Br, Y = B(OH)$_2$,
24 h, 85%
X = I, Y = B(OH)$_2$, 20 h,
87%, RT
X = Br, Y = B(MIDA),
24 h, 87%
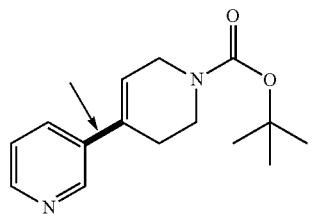
X = Br, Y = B(OH)$_2$, 16 h, 90%
X = I, Y = B(OH)$_2$, 12 h, 89%, RT
X = Br, Y = B(MIDA), 24 h, 92%
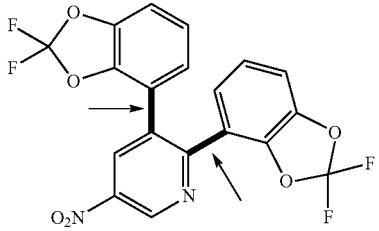
X = Cl, Br, Y = B(OH)$_2$,
38 h, 83%

TABLE 5-continued
Suzuki-Miyaura couplings between heteroaryl and heteroaryl partners
X = Cl, Y = B(OH)$_2$,
16 h, 80%, RT
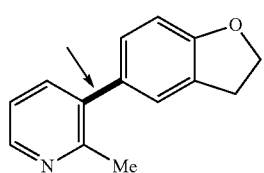
X = Br, Y = B(OH)$_2$,
20 h, RT, 94%
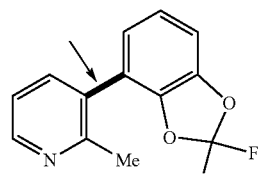
X = Br, Y = B(OH)$_2$,
24 h, 78%
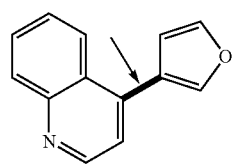
X = Br, Y = B(OH)$_2$,
13 h, 92%
X = I, Y = B(OH)$_2$,
13 h, 93%
X = Br, Y = B(MIDA),
24 h, 94%
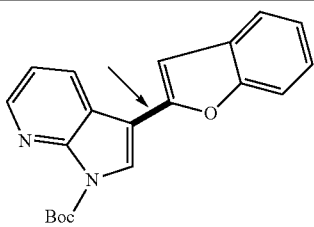
X = Cl, Y = *ArB(MIDA), 40 h, 76%
X = Br, Y = *ArB(MIDA), 33 h, 85%
X = I, Y = *ArB(MIDA), 29 h, 87%
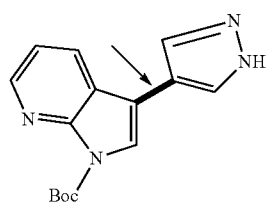
X = Br, Y = ArBpin, 28 h, 86%
X = I, Y = ArBpin, 27 h, 92%
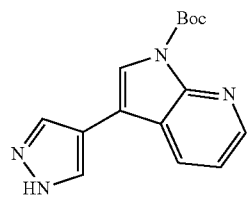
X = Br, Y = B(OH)$_2$,
28 h, 86%
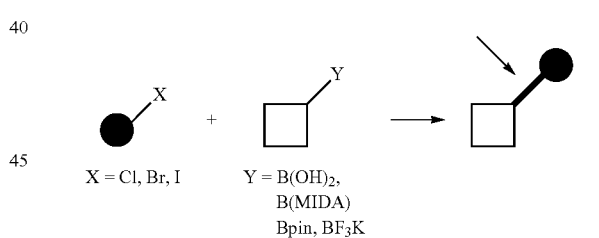
X = Cl, Br, I    Y = B(OH)$_2$,
B(MIDA)
Bpin, BF$_3$K
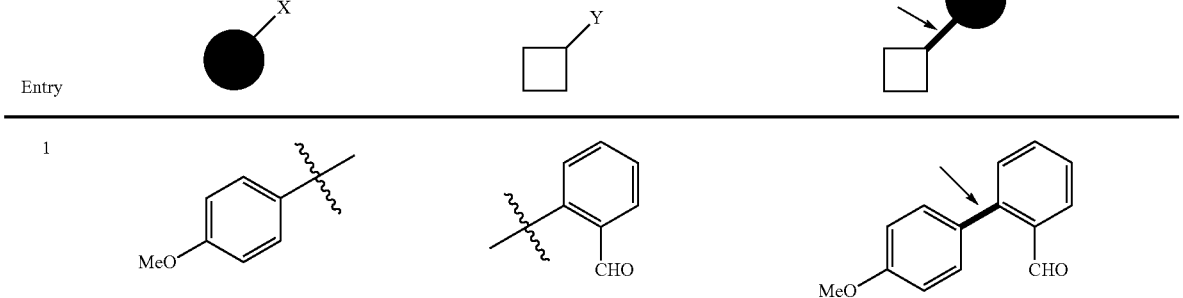
| Entry | | | |
|---|---|---|---|
| 1 | | | |

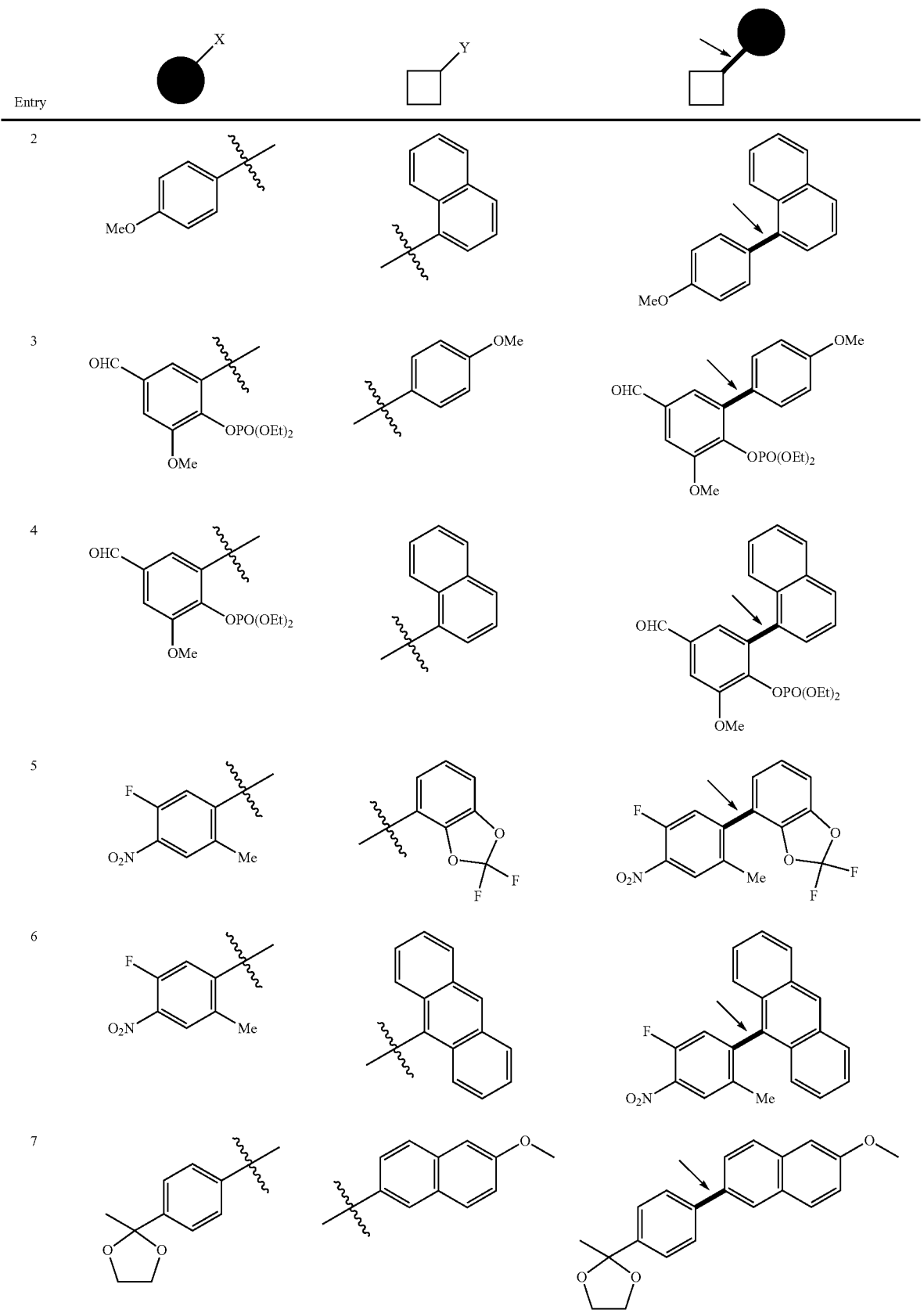

-continued
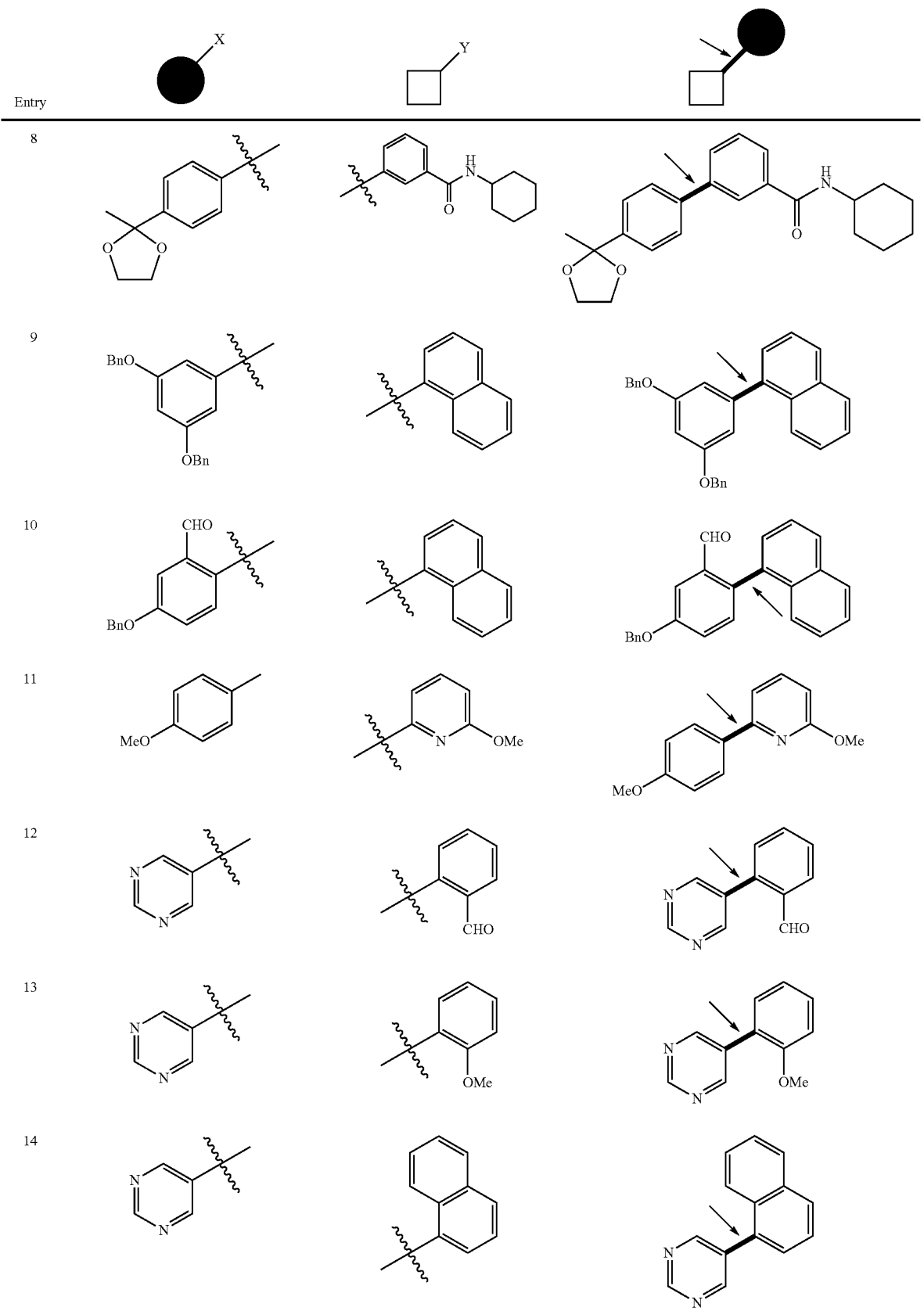

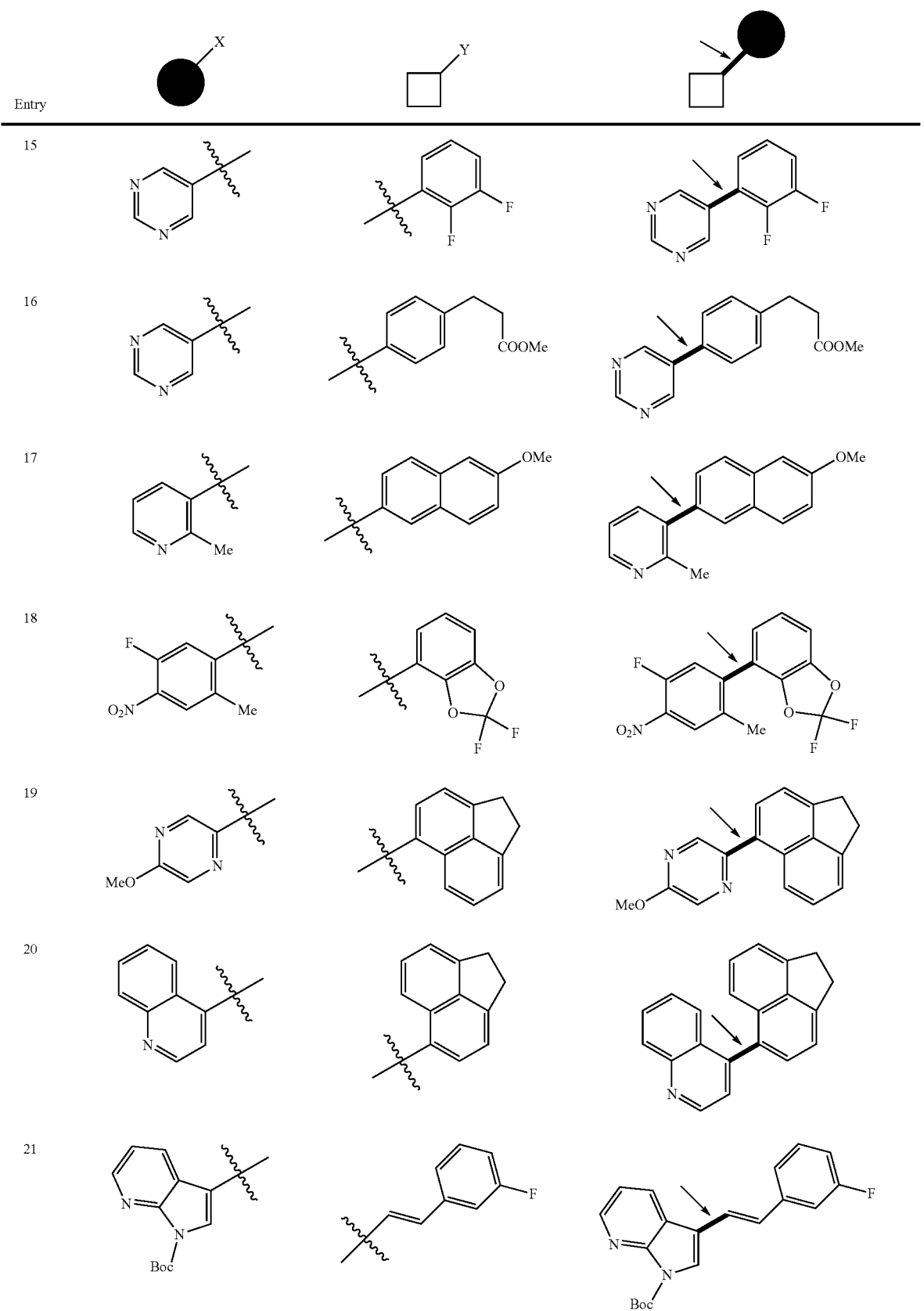

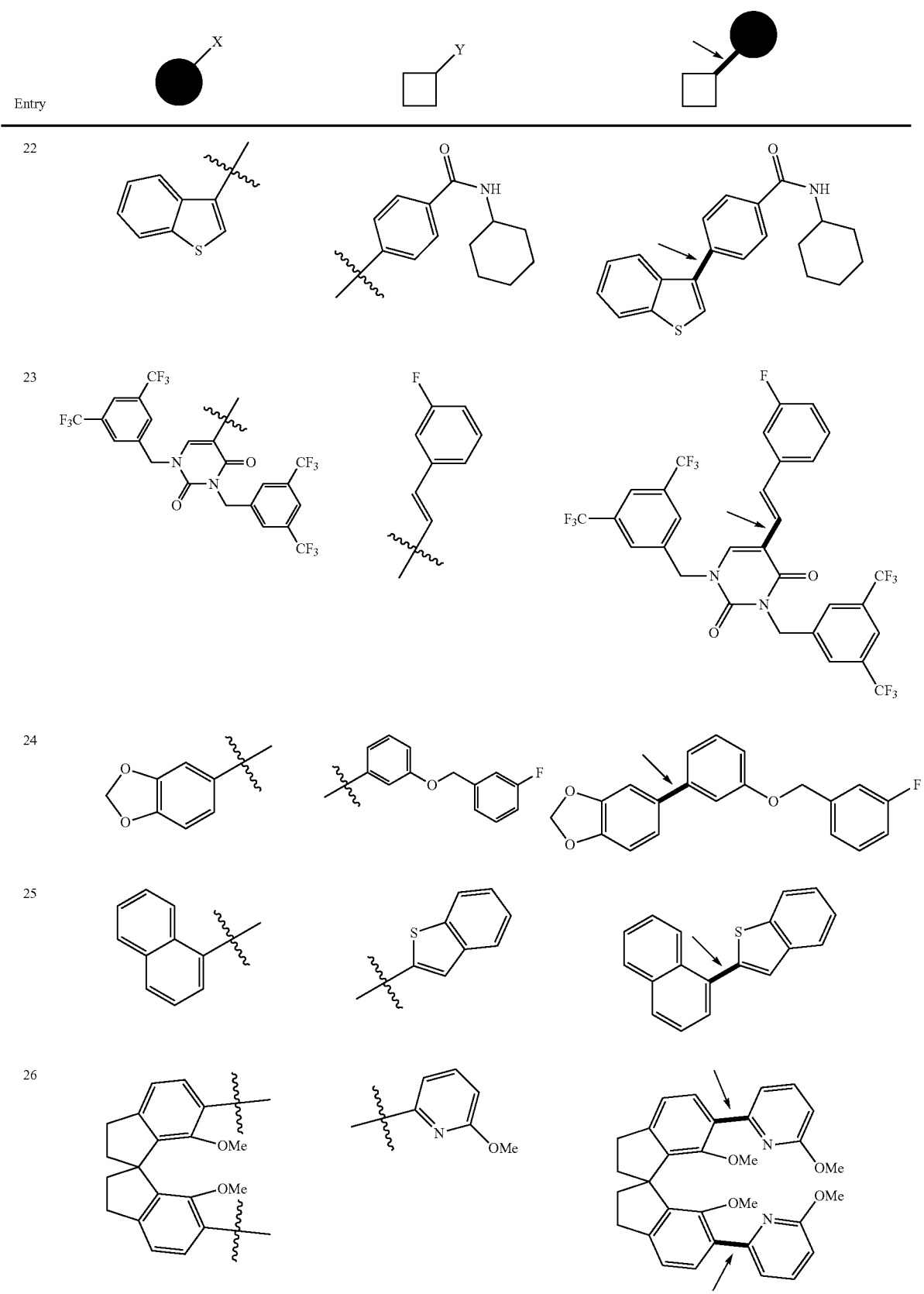

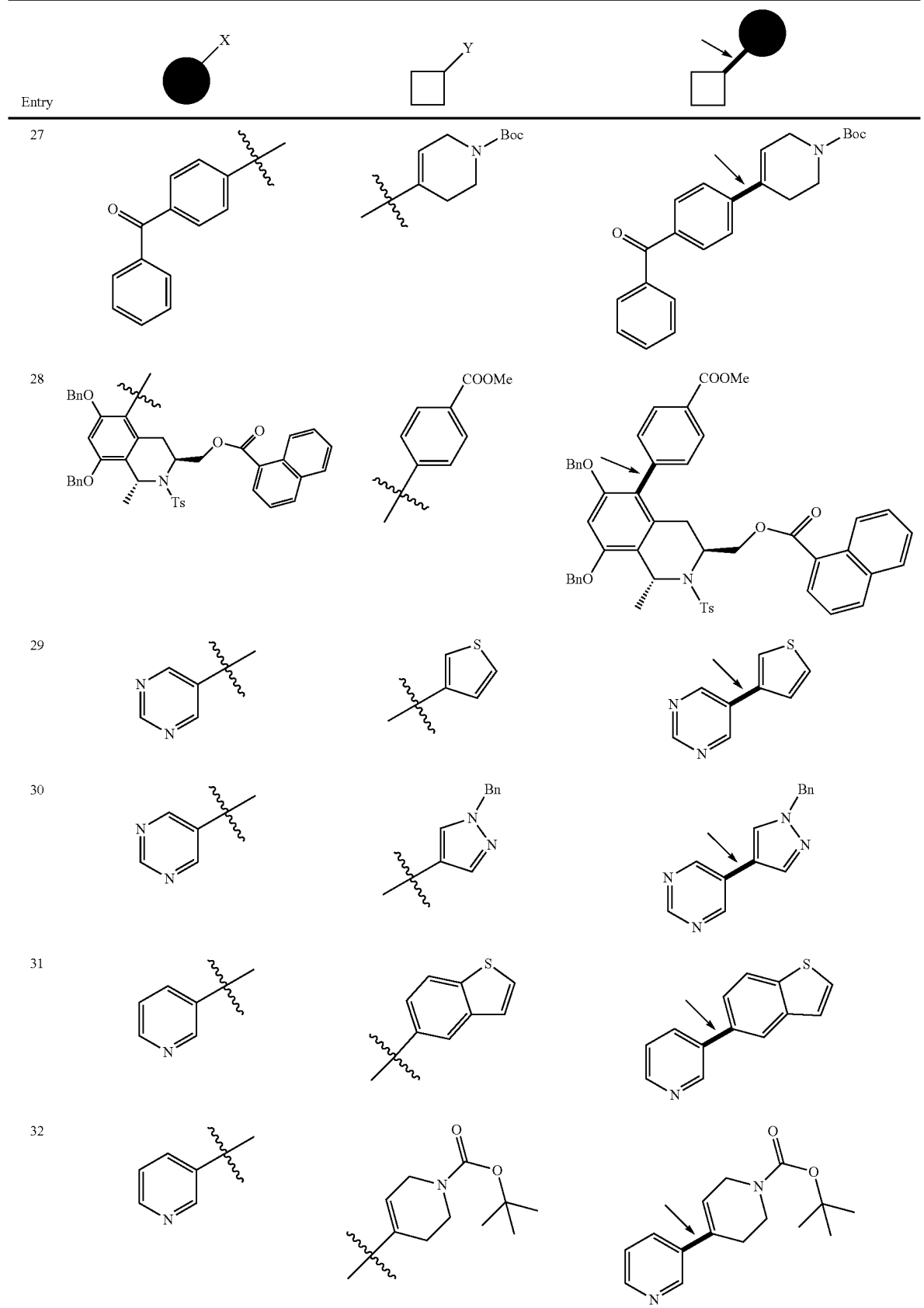

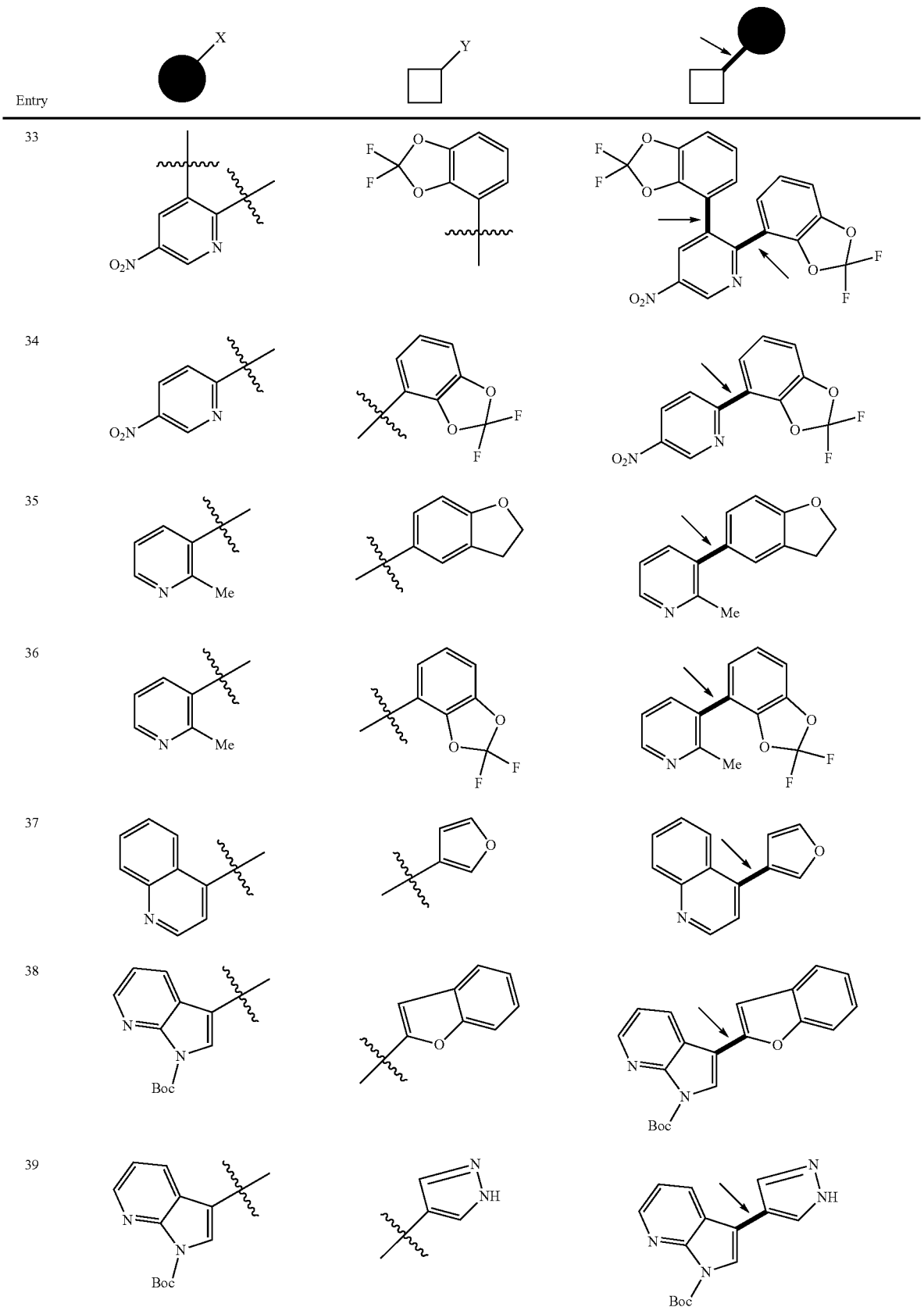

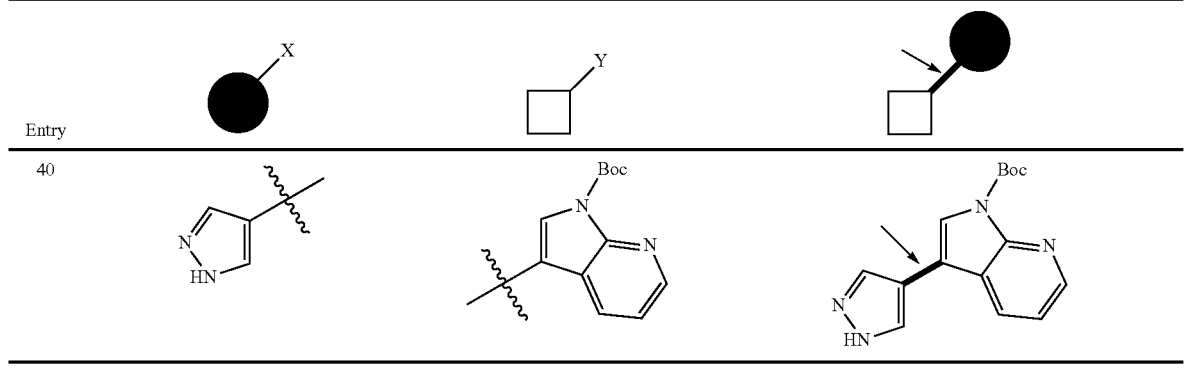

| Entry | ●—X | □—Y | ●—□ |
|---|---|---|---|
| 40 | (pyrazole) | (7-azaindole-Boc) | (coupled product) |

Preparation of Fe/Ppm Pd Nanoparticles (NPs) for SM Cross-Couplings:

In a flame dried two-neck round-bottomed flask, anhydrous pure FeCl₃ (500 mg, 3.09 mmol), SPhos (1015 mg, 2.47 mmol), and Pd(OAc)₂ (6.0 mg, 0.027 mmol) were placed under an atmosphere of dry argon. The flask was closed with a septum, and dry THF (8 mL) was added. The reaction mixture was stirred for 20 min at RT. While maintaining a dry atmosphere at RT, MeMgBr (12.4 ml, 6.18 mmol; 0.5 M solution) in THF was very slowly (1 drop/two sec) added to the reaction mixture. After complete addition of the Grignard reagent, reaction mixture was stirred for an additional 20 min at RT. An appearance of a dark-brown coloration was indicative of generation of nanomaterial. After 20 min, the mixture was quenched with a single drop of degassed water, and THF was evaporated under reduced pressure at RT followed by triturating the mixture with dry pentane to provide a green-brown-colored nanopowder (2.7 g, including material bound to THF). The nanomaterial was dried under reduced pressure at RT for 10 min. and could be used as such for catalytic reactions under micellar conditions.

Solid iron nanoparticles formed from (FeCl₃+MeMgCl) were collected and analyzed by both TEM and XPS. As illustrated in FIG. 2, TEM analysis revealed that most of the material is composed of iron rafts, along with the presence of significant amounts of carbon (48%), oxygen (22%), magnesium (9%) and chlorine (19%). The high levels of carbon and oxygen are associated with solvent (THF) trapped within these clusters; C—O shows up as a shoulder in the C1s spectrum (286.5 eV; see FIG. 2 in SI).

Remarkably, only 2.4% iron in the form of iron oxides (Fe 2p3, 710.86 eV) was found in this catalyst. Since each reaction calls for an initial 3 mol % FeCl₃, this ultimately translates into only 720 ppm Fe present within the catalyst. Analyses by AFM (FIG. 2f) revealed an atypical arrangement of iron atoms intermixed with other metals (i.e., mainly Mg). These particles display excellent shelf life (>1 month), and possess virtually identical reactivity as compared to those prepared and used in situ (Scheme 4).

TGA analysis of nanomaterial revealed about 40% total weight loss between 60-145° C. indicating the loss of THF bound within the nanocage structure. Material left after 145° C. was found to be very stable up to 380° C. In a separate experiment, loss of catalytic activity of nanomaterial was observed when pre-heated at 80° C. under vacuum for 12 h (See SI), indicating the importance of the solvent, such as THF, to perpetuate the nanocage structure.

Upon completion of a Suzuki-Miyaura coupling, in-flask extraction with a single organic solvent (e.g., i-PrOAc or MTBE) at ambient temperatures leads to crude material that can be further purified in standard fashion (Scheme 3). The remaining aqueous mixture containing both nanomicelles and nanoparticles of iron can then be recycled, using the same or different educts. Alternatively, with products that are solids, dilution with water can be followed by simple filtration to afford the targeted material, ready for recrystallization and/or final purification. The diluted filtrate can be augmented with TPGS-750-M to the original 2 weight percent level and reused, thereby creating little-to-no waste water stream. The overall E Factor associated with this chemistry, as seen previously, is only 2.95.

BRIEF DESCRIPTION OF THE FIGURE

FIG. 1 on page 1 is a graphical representation showing a new approach to the Suzuki-Miyaura coupling reaction.

FIG. 2 is a representation of a Cryo-TEM analysis of Fe/Pd nanorods in aqueous TPGS-750-M (a-c); SEM of solid nanomaterial (d-e); AFM image of solid nanomaterial (f). See SI for details.

FIG. 3 is a representation of a TGA analysis of Fe/Pd nanomaterial.

FIG. 4 is a representative figure showing a process for the recycling of the aqueous reaction mixture.

FIG. 5 shows a representative scheme of results using doped and non-doped iron nanoparticles.

FIG. 6 shows representative results of Sonogashira Coupling Reactions.

ICP analysis was performed on the product resulting from both a coupling under micellar conditions as well as that formed using traditional Pd-catalysis in an organic medium (Scheme 4). Aside from the higher yield, in one aspect of the method, avoidance of organic solvent, and far lower levels of metal used, the amount of residual palladium in the product formed in n-butanol analyzed at 160 ppm, while that found in the product using Fe/ppm Pd micellar technology was only 7 ppm Pd.

Scheme 4. ICP analysis of Pd in a product
prepared by traditional vs. micellar catalysis.

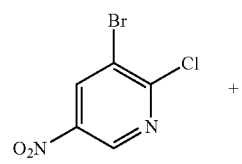

+

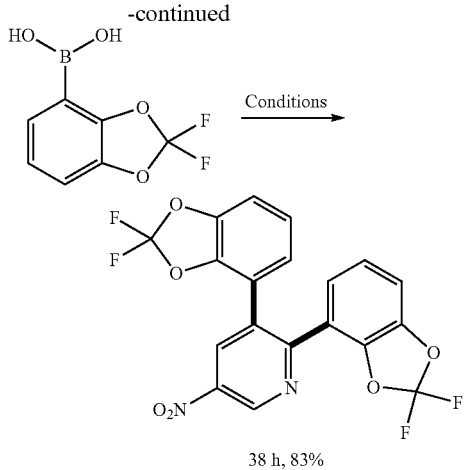

38 h, 83%

| Reaction conditions | % Yield | Pd in product (ppm) |
|---|---|---|
| This methodology Fe/Pd nanoparticles | 83 | 7 |
| Traditional methodolgy with 2-5% Pd | 72 | 160 |

The potential to apply this chemistry to an array of 1-pot sequential reactions, heteroaryl iodide 1 containing carbamate and trimethylsilyl protecting groups was generated in situ for use in a subsequent cross-coupling reaction with alkenyl tetrafluoroborate salt 2. From the cross-coupling product 3, TMS groups were removed in situ to 4, followed by Boc removal to provide intermediate 5. Final aryl amination to 6 with bromobenzene provided an overall novel one-pot route for the synthesis of this bioactive class of 2,4,5-substituted pyrazol-3-one in 68% overall yield (Scheme 5).[13]

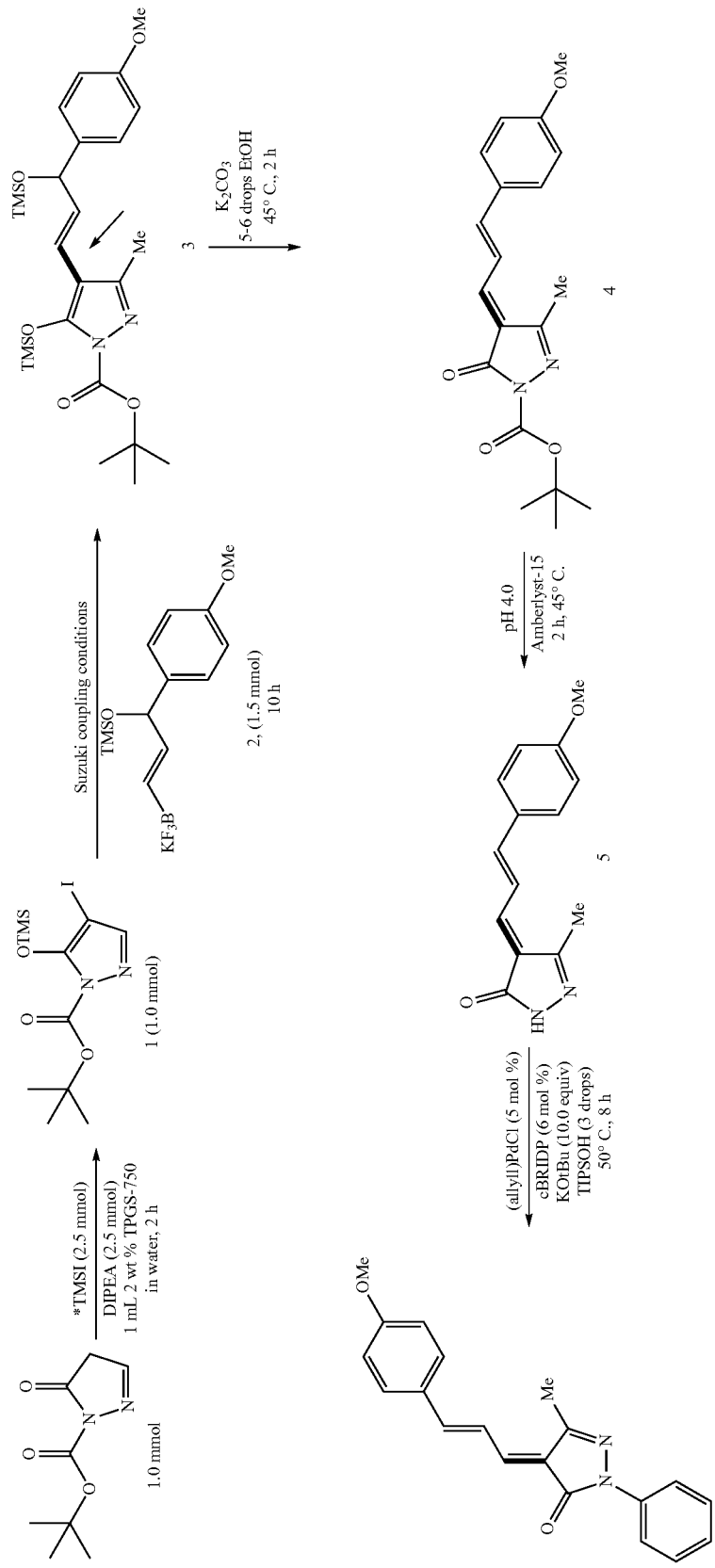

The use of the catalyst system to mediate other important Pd-catalyzed reactions, such as Sonogashira couplings, was carried out employing the coupling partners illustrated in Scheme 6. The technology may accommodate a broad array of functional groups and efficiency of reaction.

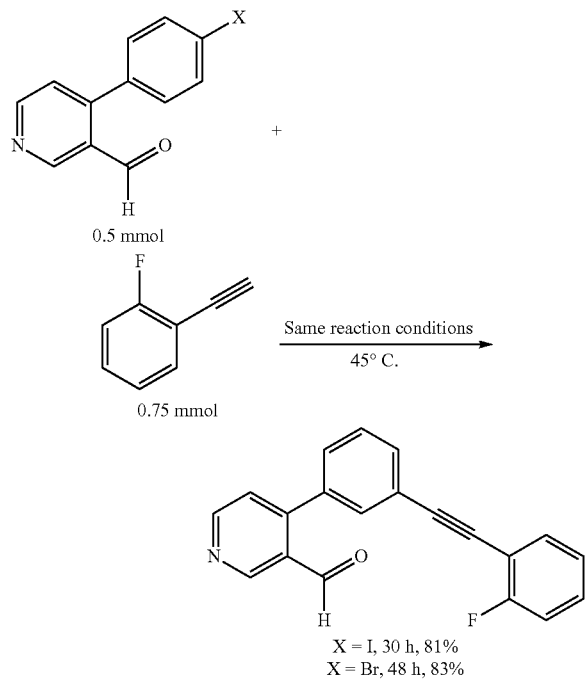

Scheme 6. The Fe/Pd catalyst in a Sonogashira reaction.

Synthesis of Active Nanoparticles:

In a flame dried two-neck round-bottomed flask, anhydrous pure $FeCl_3$ (500 mg, 3.09 mmol), XPhos (1177 mg, 2.47 mmol), and $Pd(OAc)_2$ (6.0 mg, 0.027 mmol) were placed under an atmosphere of dry argon. The flask was closed with a septum, and dry THF (10 mL) was added. The reaction mixture was stirred for 20 min at RT. While maintaining a dry atmosphere at RT, MeMgCl (12.4 ml, 6.18 mmol; 0.5 M solution) in THF was very slowly (1 drop/two sec) added to the reaction mixture. After complete addition of the Grignard reagent, the reaction mixture was stirred for an additional 10 min at RT. An appearance of a dark-brown coloration was indicative of generation of nanomaterial.

After 20 min, the mixture was quenched with a 0.1 mL of degassed water, and THF was evaporated under reduced pressure at RT followed by triturating the mixture with dry pentane to provide a light brown-colored nanopowder (2.82 g, including material bound to THF). The nanomaterial was dried under reduced pressure at RT for 10 min and could be used as such for Sonogashira reactions under micellar conditions.

General Procedure for Sonogashira Reactions:
a) Using In Situ Formation of Catalyst Fe/ppm Pd nanoparticle formation as well as Sonogashira reactions were air sensitive, all reactions were ran under argon. Pure $FeCl_3$ (97%, source Sigma-Aldrich) was doped with 320 ppm of palladium using 0.005 M solution of $Pd(OAc)_2$ (source, Oakwood Chemicals) in dry $CH_2Cl_2$ when nanoparticles were in situ formed.

In a flame dried 4 mL microwave reaction vial, $FeCl_3$ (4.1 mg, 5 mol %) containing ppm levels of palladium (ca. 350 ppm), XPhos (12 mg, 5 mol %) was added under anhydrous conditions. The reaction vial was closed with a rubber septum and the mixture was evacuated-and-backfilled with argon three times. Dry $CH_2Cl_2$ (1.0 mL) was added to the vial and the mixture was stirred for 30 min at RT, after which, while maintaining the inert atmosphere, $CH_2Cl_2$ was evaporated under reduced pressure. MeMgCl in THF (0.2 mL, 10 mol %; 0.1 M) was added to the reaction mixture, which was stirred at RT for one min. A freshly degassed aqueous solution of 2 wt % TPGS-750-M (1.0 mL) was added to the vial followed by sequential addition of aryl bromide or iodide (0.5 mmol), terminal alkyne (0.75 mmol, 1.5 equiv), and triethylamine (139 µL, 1.0 mmol, 2.0 equiv). The vial was closed with a rubber septum and evacuated-and-back-filled with argon three times. The mixture was stirred vigorously at 45° C. for the desired time period.

After complete consumption of starting material, as monitored by TLC or GCMS, the reaction mixture was allowed to cool to RT. EtOAc or MTBE (1 mL) or 5% EtOAc/MTBE was added to the reaction mixture, which was stirred gently for 5 min. Stirring was stopped and the magnetic stir bar was removed. The organic layer was separated with the aid of a centrifuge and then dried over anhydrous sodium sulfate. The solvent was then evacuated under reduced pressure to obtain crude material which was purified by flash chromatography over silica gel using EtOAc/hexanes or ether/hexanes as eluent.

a) Using in Isolated Catalyst:

Under the argon atmosphere, 30 mg nanoparticles were added in to a flame dried 4 mL reaction vial. Reaction vial was closed with a rubber septum and 1.0 mL freshly degassed aqueous solution of 2 wt % TPGS-750-M was added to it via syringe. Reaction mixture was stirred for a minute at RT followed by sequential addition of aryl bromide or iodide (0.5 mmol), terminal alkyne (0.75 mmol, 1.5 equiv), and triethylamine (139 µL, 1.0 mmol, 2.0 equiv). The vial was closed with a rubber septum and evacuated-and-back-filled with argon three times. The mixture was stirred vigorously at 45° C. for the desired time period.

After complete consumption of starting material, as monitored by TLC or GCMS, the reaction mixture was allowed to cool to RT. EtOAc or MTBE (1 mL) or 5% EtOAc/MTBE was added to the reaction mixture, which was stirred gently for 5 min. Stirring was stopped and the magnetic stir bar was removed. The organic layer was separated with the aid of a centrifuge and then dried over anhydrous sodium sulfate. The solvent was then evacuated under reduced pressure to obtain crude material which was purified by flash chromatography over silica gel using EtOAc/hexanes or ether/hexanes as eluent.

Synthesis of Active Nanoparticles:

In a flame dried two-neck round-bottomed flask, anhydrous pure $FeCl_3$ (500 mg, 3.09 mmol), XPhos (1180 mg, 2.47 mmol), and $Pd(OAc)_2$ (6.0 mg, 0.027 mmol) were placed under an atmosphere of dry argon. The flask was closed with a septum, and dry THF (10 mL) was added. The reaction mixture was stirred for 20 min at RT. While maintaining a dry atmosphere at RT, MeMgCl (12.4 ml, 6.18 mmol; 0.5 M solution) in THF was very slowly (1 drop/two sec) added to the reaction mixture. After complete addition of the Grignard reagent, the reaction mixture was stirred for an additional 10 min at RT. An appearance of a dark-brown coloration was indicative of generation of nanomaterial.

After 20 min, the mixture was quenched with a 0.1 mL of degassed water, and THF was evaporated under reduced pressure at RT followed by triturating the mixture with dry pentane to provide a light brown-colored nanopowder (2.82 g, including material bound to THF). The nanomaterial was dried under reduced pressure at RT for 10 min and could be used as such for Sonogashira reactions under micellar conditions.

General Procedure for Sonogashira Reactions:

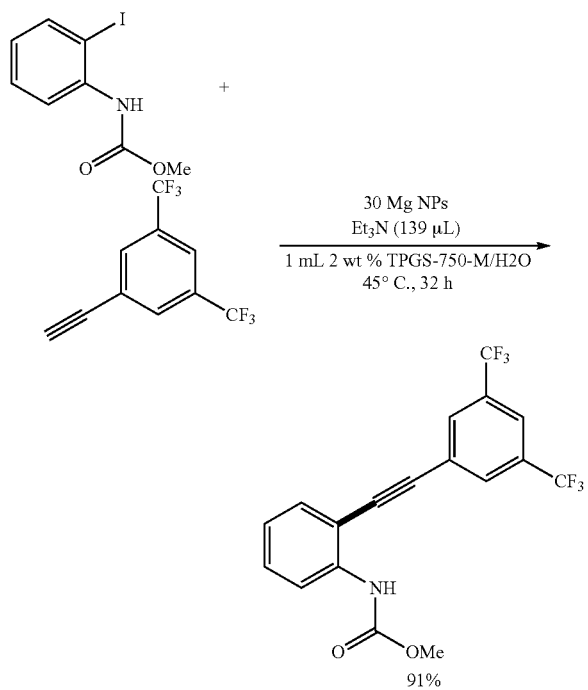

a) Using In Situ Formation of Catalyst:

Fe/ppm Pd nanoparticle formation as well as Sonogashira reactions were air sensitive; all reactions were ran under argon. Pure $FeCl_3$ (97%, source Sigma-Aldrich) was doped with 320 ppm of palladium using 0.005 M solution of $Pd(OAc)_2$ (Oakwood Chemicals) in dry $CH_2Cl_2$ when nanoparticles were in situ formed.

In a flame dried 4 mL microwave reaction vial, $FeCl_3$ (4.1 mg, 5 mol %) containing ppm levels of palladium (ca. 350 ppm), XPhos (12 mg, 5 mol %) was added under anhydrous conditions. The reaction vial was closed with a rubber septum and the mixture was evacuated-and-backfilled with argon three times. Dry $CH_2Cl_2$ (1.0 mL) was added to the vial and the mixture was stirred for 30 min at RT, after which, while maintaining the inert atmosphere, $CH_2Cl_2$ was evaporated under reduced pressure. MeMgCl in THF (0.2 mL, 10 mol %; 0.1 M) was added to the reaction mixture, and stirred at RT for one min. A freshly degassed aqueous solution of 2 wt % TPGS-750-M (1.0 mL) was added to the vial followed by sequential addition of N-(2-iodophenyl) acetamide (138 mg, 0.5 mmol), 1-ethynyl-3,5-bis(trifluoromethyl)benzene (179 mg, 0.75 mmol, 1.5 equiv) and triethylamine (139 µL, 1.0 mmol, 2.0 equiv). The vial was closed with a rubber septum and evacuated-and-back-filled with argon 3 times. The mixture was stirred vigorously at 45° C. for the 32 h.

After complete consumption of starting material by TLC or GCMS, the reaction mixture was allowed to cool to RT. 2 mL EtOAc was added to the mixture, which was stirred gently for 5 min. Stirring was stopped and the magnetic stir bar was removed. The organic layer was separated with the aid of a centrifuge. Similar extraction procedure was repeated and combined organic layer was dried over anhydrous sodium sulfate. The solvent was then evacuated under reduced pressure to obtain crude material which was purified by flash chromatography over silica gel using EtOAc/hexanes (1:49) as eluent. $R_f$ 0.35 in EtOAc/hexanes, white solid, yield 91% (175 mg). $^1H$ NMR (400 MHz, $CDCl_3$) δ 8.18 (d, J=8.8 Hz, 1H), 7.97 (s, 2H), 7.86 (s, 1H), 7.50 (dd, J=8.4 and 1.2 Hz, 1H), 7.43-7.39 (m, 1H), 7.32 (br. s, 1H), 7.06 (t, J=8.0 Hz, 1H), 3.83 (s, 3H); $^{19}F$ NMP (376 MHz, $CDCl_3$) δ -63.2; $^{13}C$ NMR (101 MHz, $CDCl_3$) δ -153.7, 139.4, 132.4, 132.3 (q, $J_{(C,F)}$=34 Hz), 131.6, 131.5, 131.0, 125.0, 123.0, 123 (q, $J_{(C,F)}$=274 Hz), 122.2 (septet, $J_{(C,F)}$=3.8 Hz), 118.3, 110.3, 93.0, 87.9, and 52.7. ppm.

a) Using in Isolated Catalyst:

Under the argon atmosphere, 30 mg nanoparticles were added in to a flame dried 4 mL reaction vial. Reaction vial was closed with a rubber septum and 1.0 mL freshly degassed aqueous solution of 2 wt % TPGS-750-M was added via syringe. Reaction mixture was stirred for a minute at RT followed by sequential addition of N-(2-iodophenyl) acetamide (131 mg, 0.5 mmol), 1-ethynyl-3,5-bis(trifluoromethyl)benzene (179 mg, 0.75 mmol, 1.5 equiv), and triethylamine (139 µL, 1.0 mmol, 2.0 equiv). The vial was closed with a rubber septum and evacuated-and-back-filled with argon three times. The mixture was stirred vigorously at 45° C. for 32 hours.

After complete consumption of starting material by TLC or GCMS, the reaction mixture was allowed to cool to RT. 2 mL EtOAc was added to the mixture and stirred for 5 min. Stirring was stopped and the magnetic stir bar was removed. The organic layer was separated with the aid of a centrifuge. Similar extraction procedure was repeated and combined organic layer was dried over anhydrous sodium sulfate. The solvent was then evacuated under reduced pressure to obtain crude material which was purified by flash chromatography over silica gel using EtOAc/hexanes (1:49) as eluent. $R_f$ 0.35 in EtOAc/hexanes, white solid, yield 91% (175 mg). $^1H$ NMR (400 MHz, $CDCl_3$) δ 8.18 (d, J=8.8 Hz, 1H), 7.97 (s, 2H), 7.86 (s, 1H), 7.50 (dd, J=8.4 and 1.2 Hz, 1H), 7.43-7.39 (m, 1H), 7.32 (br. s, 1H), 7.06 (t, J=8.0 Hz, 1H), 3.83 (s, 3H); $^{19}F$ NMP (376 MHz, $CDCl_3$) δ -63.2; $^{13}C$ NMR (101 MHz, $CDCl_3$) δ -153.7, 139.4, 132.4, 132.3 (q, $J_{(C,F)}$=34 Hz), 131.6, 131.5, 131.0, 125.0, 123.0, 123 (q, $J_{(C,F)}$=274 Hz), 122.2 (septet, $J_{(C,F)}$=3.8 Hz), 118.3, 110.3, 93.0, 87.9 and 52.7. ppm.

As disclosed herein, a new catalyst system may be employed for valuable cross-couplings or cross-coupling reactions that utilizes iron nanoparticles doped naturally, or externally, with ppm levels of Pd. Coupling reactions, such as the Suzuki-Miyaura reactions studied are enabled by micellar catalysis that provides the nano reactors that house and deliver the reaction partners to the catalyst. The conditions are very mild, while efficiencies are high. Both the catalyst and aqueous medium in which the reactions occur are not only recyclable, but also environmentally responsible based on the very low E Factors associated with this chemistry.

The foregoing examples of the related art and limitations are intended to be illustrative and not exclusive. Other limitations of the related art will become apparent to those of skill in the art upon a reading of the specification and a study of the drawings or figures as provided herein. In addition to the exemplary embodiments, aspects and variations described above, further embodiments, aspects and variations will become apparent by reference to the drawings and figures and by examination of the following descriptions.

Definitions Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $C_1$-$C_{20}$alkyl or $C_{1-20}$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $C_1$-$C_{20}$alkyl, for example) and/or aryl group (as in $C_5$-$C_{14}$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$C_1$-$C_3$ alkylene- or —$C_1$-$C_3$alkylenyl-.

The term "alkynyl" refers to a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups as disclosed herein, including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl and the like. The term "heterocycloalkyl" is a type of cycloalkyl group and is included within the meaning of the term "cycloalkyl," where at least one of the carbon atoms of the ring is replaced with a heteroatom such as, but not limited to, nitrogen, oxygen, sulfur or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

"Halogen" or "halo" means fluorine, chlorine, bromine or iodine.

The terms "heterocycle" or "heterocyclyl," as used herein can be used interchangeably and refer to single and multi-cyclic aromatic or non-aromatic ring systems in which at least one of the ring members is other than carbon. The term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. A heterocyclyl group can also be a $C_2$ heterocyclyl, $C_2$-$C_3$ heterocyclyl, $C_2$-$C_4$ heterocyclyl, $C_2$-$C_5$ heterocyclyl, $C_2$-$C_6$ heterocyclyl, $C_2$-$C_7$ heterocyclyl, $C_2$-$C_8$ heterocyclyl, $C_2$-$C_9$ heterocyclyl, $C_2$-$C_{10}$ heterocyclyl, $C_2$-$C_{11}$ heterocyclyl, and the like up to and including a $C_2$-$C_{18}$ heterocyclyl. For example, a $C_2$ heterocyclyl comprises a group which has two carbon atoms and at least one heteroatom, including, but not limited to, aziridinyl, diazetidinyl, dihydrodiazetyl, oxiranyl and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like.

A "heteroaryl," refers to an aromatic group that has at least one heteroatom incorporated within the ring of the aromatic group. Examples of heteroatoms include, but are not limited to, nitrogen, oxygen, sulfur and phosphorus. The heteroaryl group can be substituted or unsubstituted. The heteroaryl group can be substituted with one or more groups including, alkyl, cycloalkyl, alkoxy, amino, ether, halide, hydroxy, nitro, silyl or thiol. Heteroaryl groups can be monocyclic, or fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Other examples of heteroaryl groups include pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl and pyrido[2,3-b]pyrazinyl.

The term "pseudohalides", by themselves or as part of another substituent, refers to species resembling halides in their charge and reactivity, and are generally a good leaving group in a reaction, such as a substitution reaction. Examples are azides (NNN—), isocyanate (—NCO), isocyanide, (CN—), triflate (—OSO$_2$SF$_3$) and mesylate (CH$_3$SO$_2$O—).

"Substituted or unsubstituted" or "optionally substituted" means that a group such as, for example, alkyl, aryl, heterocyclyl, $C_1$-$C_8$cycloalkyl, heterocyclyl($C_1$-$C_8$)alkyl, aryl ($C_1$-$C_8$)alkyl, heteroaryl, heteroaryl($C_1$-$C_8$)alkyl, and the like, unless specifically noted otherwise, may be unsubstituted or, may substituted by 1, 2 or 3 substituents selected from the group such as halo, nitro, trifluoromethyl, trifluoromethoxy, methoxy, carboxy, —NH$_2$, —OH, —OMe, —SH, —NHCH$_3$, —N(CH$_3$)$_2$, —SMe, cyano and the like.

REFERENCES

[1] a) C. C. C. J Seechurn et al., *Angew. Chem., Int. Ed.* 2012, 51, 5062-5085; b) H. Li et al., *ACS Catal.* 2012, 2, 1147-1164.

[2] a) S. Z. Tasker et al., *Nature* 2014, 509, 299-309; b) S. D. Ramgren et al., *Org. Lett.* 2013, 15, 3950-3953; c) F.-S. Han, *Chem. Soc. Rev.* 2013, 42, 5270-5298; d) F. Gonzalez-Bobes et al., *J. Am. Chem. Soc.* 2006, 128, 5360-5361; e) L. Hie et al., *J. Chem. Educ.* 2014; f) A. H. Christian et al., Organometallics 2014, 33, 2134-2137; g) L. Chen et al., *Eur. J. Org. Chem.* 2014, 2014, 4953-4957; h) X. Wu et al., *J. Am. Chem. Soc.* 2014, 136, 1789-1792; i) J. C. Tellis et al., *Science* 2014, 345, 433-436.

[3] a) S. K. Gurung et al., *Org. Lett.* 2014, 16, 1264-1267; b) Y. Zhou et al., *Angew. Chem., Int. Ed.* 2014, 126, 3543-3547; c) N. He et al., *Org. Lett.* 2015; d) L. Cheng et al., *RSC Adv.* 2014, 4, 44312-44316; e) Y.-Y. Sun et al., *Chem. Commun.* 2014, 50, 11060-11062; f) C.-T. Yang et al., *Angew. Chem., Int. Ed.* 2011, 50, 3904-3907; g) J. Mao et al., *Tetrahedron* 2008, 64, 3905-3911.

[4] a) N. Zhang et al., *J. Org. Chem.* 2012, 77, 5956-5964; b) M. B. Thathagar et al., *J. Am. Chem. Soc.* 2002, 124, 11858-11859; c) M. R. Netherton et al., *Adv. Synth. Catal.* 2004, 346, 1525-1532; d) G. D. Allred et al., *J. Am. Chem. Soc.* 1996, 118, 2748-2749; e) L. Xu et al., *Org. Lett.* 2010, 12, 884-887.

[5] B. H. Lipshutz, S. Ghorai, A. R. Abela, R. Moser, T. Nishikata, C. Duplais, A. Krasovskiy, R. D. Gaston, R. C. Gadwood, *J. Org. Chem.* 2011, 76, 4379-4391.

[6] a) M. A. Düfert et al., *J. Am. Chem. Soc* 0.2013, 135, 12877-12885; b) Y. Yang, S. L. Buchwald, *J. Am. Chem. Soc.* 2013, 135, 10642-10645.

[7] a) R. Martin et al., *Acc. Chem. Res.* 2008, 41, 1461-1473; b) B. Bhayana et al. *Org. Lett.* 2009, 11, 3954-3957.

[8] a) A. J. J. Lennox et al., *Chem. Soc. Rev.* 2014, 43, 412-443; b) A. Bonet et al. *Nat Chem* 2014, 6, 584-589; c) M. K. Tse, J.-Y. Cho, M. R. Smith, *Org. Lett* 2001, 3, 2831-2833; d) B. H. Lipshutz, R. Moser, K. R. Voigtritter, *Isr. J. Chem.* 2010, 50, 691-695.

[9] a) N. A. Isley, F. Gallou, B. H. Lipshutz, *J. Am. Chem. Soc.* 2013, 135, 17707-17710; b) S. J. Lee et al., *Angew. Chem., Int. Ed.* 2010, 49, 8860-8863; c) A. J. Lennox et al. *Isr. J. Chem.* 2010, 50, 664-674.

[10] a) W. K. Chow et al., *J. Org. Chem.* 2010, 75, 5109-5112; b) G. A. Molander et al., *J. Org. Chem.* 2006, 71, 2493-2498.

[11] a) T. H. Bointon et al., *Nano Lett.* 2014, 14, 1751-1755; b) S. L. Buchwald, C. Bolm, *Angew. Chem., Int. Ed.* 2009, 48, 5586-5587.

[12] a) C. L. Chun et al., *Environ. Sci. Technol.* 2010, 44, 5079-5085; b) Y.-P. Sun et al., *Adv. Colloid Interface Sci.* 2006, 120, 47-56; c) I. Thome, A. Nijs, C. Bolm, *Chem. Soc. Rev.* 2012, 41, 979-987.

[13] a) P. N. Dube et al., *Chem. Biol. Drug Des.* 2014, 84, 409-419; b) N. Kumar et al., *Arab. J. Chem.*; c) B. F. Abdel-Wahab et al, *Archiv der Pharmazie* 2008, 341, 734-739; d) R. Wizinger et al. *Helv. Chim. Acta* 1955, 38, 372-380.

The entire disclosures of all documents cited throughout this application are incorporated herein by reference. While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

What is claimed is:

1. An aqueous micellar composition in a reaction solvent for enabling cross-coupling reactions containing organometallic nanoparticles (NPs) as catalyst, comprising:
   a) an element selected from the group consisting of Fe, C, H, O, Mg, and a halide, or the entire combination thereof; and
   b) palladium (Pd), or at least one other metal selected from the group consisting of Pt, Au, Ni, Co, Cu and Mn, or a mixture thereof; wherein the catalyst (NPs) is prepared from a reduction of an iron salt or an iron complex in a solvent and in the presence of a ligand using a reducing agent.

2. The aqueous micellar composition of claim 1, wherein the iron is selected from the group consisting of a Fe(II) or Fe(III) salt, a Fe(II) salt precursor or Fe(III) salt precursor.

3. The aqueous micellar composition of claim 1, wherein the Pd is naturally present in the iron salt or the iron complex in amounts less than or equal to 1 ppm, 10 ppm, 50 ppm, 100 ppm, 200 ppm, 300 ppm, 400 ppm or 500 ppm relative to the iron salt or iron complex.

4. The aqueous micellar composition of claim 3, where the amount of Pd present is controlled by external addition of a palladium salt to an iron salt.

5. The aqueous micellar composition of claim 3, wherein the reducing reagent is a Grignard reagent selected from the group consisting of MeMgCl, MeMgBr, MeMgI, EtMgCl, EtMgBr, EtMgI, i-PrMgCl, i-PrMgBr, i-PrMgI, PhMgCl, PhMgBr, PhMgI, n-hexyl-MgBr, n-hexyl-MgCl, n-hexyl-MgBr, n-hexyl-MgCl, n-hexyl-MgI, NaBH$_4$, liBH$_4$, BH$_3$-THF, BH$_3$—SMe$_2$, borane, DIBAL-H and LiAlH$_4$; and mixtures thereof.

6. The aqueous micellar composition of claim 1 further comprising a surfactant, wherein the surfactant is selected from the group consisting of TPGS-500, TPGS-500-M, TPGS-750, TPGS-750-M, TPGS-1000 and TPGS-1000-M, Nok and PTS, or a mixture thereof.

7. The aqueous micellar composition of claim 1, further comprising a ligand selected from the group consisting of $PPh_3$, $(o\text{-}Tol)_3P$, $(p\text{-}Tol)_3P$, dppf, dtbpf, BiDime, Tangphos, IMes, IPr, SPhos, t-BuSPhos, XPhos, t-BuXPhos, BrettPhos and t-BuBrettPhos, and HandaPhos or an analog thereof.

8. The aqueous micellar composition of claim 1, wherein the iron metal complex as nanoparticles is heterogeneous and can be isolated from the composition, stored and recycled.

9. The composition of claim 1, wherein the reaction solvent is water, and the reaction solvent further comprising an organic solvent, wherein the organic co-solvent is present in at least 5%, 10%, 20%, 30%, 40%, 50%, 70%, 80% or at least 90% wt/wt.

\* \* \* \* \*